US010006035B2

(12) United States Patent
Ye et al.

(10) Patent No.: US 10,006,035 B2
(45) Date of Patent: Jun. 26, 2018

(54) USE OF NON-AGROBACTERIUM BACTERIAL SPECIES FOR PLANT TRANSFORMATION

(71) Applicant: MONSANTO TECHNOLOGY LLC, St. Louis, MO (US)

(72) Inventors: Xudong Ye, Madison, WI (US); Junjiang Shen, Madison, WI (US); Edward Williams, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 70 days.

(21) Appl. No.: 15/151,383

(22) Filed: May 10, 2016

(65) Prior Publication Data

US 2016/0319289 A1    Nov. 3, 2016

Related U.S. Application Data

(60) Continuation of application No. 14/298,739, filed on Jun. 6, 2014, now Pat. No. 9,365,859, which is a continuation of application No. 12/975,259, filed on Dec. 21, 2010, now abandoned, which is a division of application No. 11/749,583, filed on May 16, 2007, now Pat. No. 7,888,552.

(60) Provisional application No. 60/800,872, filed on May 16, 2006.

(51) Int. Cl.
  *C12N 15/84*  (2006.01)
  *C12R 1/41*   (2006.01)
  *C12N 15/82*  (2006.01)
  *G01N 33/50*  (2006.01)

(52) U.S. Cl.
  CPC ..... *C12N 15/8202* (2013.01); *C12N 15/8205* (2013.01); *C12R 1/41* (2013.01); *G01N 33/5097* (2013.01)

(58) Field of Classification Search
  None
  See application file for complete search history.

(56) References Cited

U.S. PATENT DOCUMENTS

| | | | |
|---|---|---|---|
| 5,077,209 | A | 12/1991 | O'Gara et al. |
| 5,427,785 | A | 6/1995 | Ronson et al. |
| 6,384,301 | B1 | 5/2002 | Martinell et al. |
| 7,002,058 | B2 | 2/2006 | Martinell et al. |
| 7,601,536 | B2 | 10/2009 | Rommens et al. |
| 7,682,829 | B2 | 3/2010 | Cai et al. |
| 7,888,552 | B2 | 2/2011 | Ye et al. |
| 2003/0046733 | A1 | 3/2003 | Dias et al. |
| 2005/0289667 | A1 | 12/2005 | Jefferson |
| 2005/0289672 | A1 | 12/2005 | Jefferson |
| 2006/0070137 | A1 | 3/2006 | Rommens et al. |

FOREIGN PATENT DOCUMENTS

| | | |
|---|---|---|
| EP | 0 224 287 | 6/1987 |
| WO | WO 1992-000377 | 1/1992 |
| WO | WO 2006-004914 | 1/2006 |

OTHER PUBLICATIONS

Weller et al. Archives of Microbiology 178(5): 338-343.*
Bhattacharjee et al., "A segment of a plasmid gene required for conjugal transfer encodes a site specific, single-strand DNA endonuclease and ligase," *Nucleic Acids Res.*, 19:1129-1137, 1991.
Bravo-Angel et al., "Bacterial conjugation protein MobA mediates integration of complex DNA structures into plant cells," *J. Bacteriol.*, 181:5758-5765, 1999.
Brom et al., Meeting Abstracts, Plasmid Biology 98: International Symposium on Plasmid Biology, Merida, Mexico, Oct. 10-16, 1998, *Plasmid*, 41:141-177, 1999.
Broothaerts et al., "Gene transfer to plants by diverse species of bacteria," *Nature*, 433:629-633, 2005.
Buchanan-Wollaston et al., "The mob and oriT of a bacterial plasmid promote its transfer to plants," *Nature*, 328:172-175, 1987.
Chilton, "Adding diversity to plant transformation," *Nature Biotechnology*, 23(3):309-310, 2005.
Chung et al., "Agrobacterium is not alone: gene transfer to plants by viruses and other bacteria," *Trends in Plant Sci.*, 11(1):1-4, 2006.
Dale, et al., "Gene transfer with subsequent removal of the selection gene from the host genome," *Proceedings of the National Academy of Sciences*, 88(23):10558-10562, 1991.
Danino et al., "Recipient-induced transfer of the symbiotic plasmid pRL1JI in Rhizobium leguminosarum bv. Viciae is regulated by a quorum-sensing relay," *Mol. Microbiol.*, 50(2):511-525, 2003.
Dorrington et al., "The broadhost-range plasmid PTF-FC2 requires a primase-like protein for autonomous replication in *Echerichia coli*," *Gene*, 108:7-14, 1991.
Dube et al., "Agrobacterium tumefaciens-mediated transformation of plants by the pTF-FC2 plasmid is efficient and strictly dependent on the MobA protein," *Plant Mol. Biol.*, 55(4):531-539, 2004.
Dube et al., "Conjugal transfer of plasmid pTF-FC2 from Agrobacterium to plant cells in the absence of T-DNA borders," *Plasmid*, 50:1-11, 2003.
Escudero et al., "VirD4-independent transformation by CloDF13 evidences an unknown factor required for the genetic colonization of plants via Agrobacterium," *Molecular Microbiology*, 47:891-901, 2003.
Farrand et al., "Agrobacterium is a definable genus of the family Rhizobiaceae," *Int. J. Syst. Evol. Microbiol.*, 53:1681-1687, 2003.
Farrand et al., "The tra region of the nopaline-type Ti plasmid is a chimera with elements related to the transfer systems of RSF1010, RP4 and F," *J. of Bacteriology*, 178(14):4233-4247, 1996.

(Continued)

*Primary Examiner* — David T Fox
(74) *Attorney, Agent, or Firm* — Dentons US LLP; David Lanzotti Esq.

(57) ABSTRACT

The invention relates to methods for Rhizobia-mediated genetic transformation of plant cells, including soybean, canola, corn, and cotton cells. These include both VirD2-dependent and VirD2-independent methods. Bacterial species utilized include strains of *Rhizobium* sp., *Sinorhizobium* sp., and *Mesorhizobium* sp. Vectors for use in such transformation are also disclosed.

23 Claims, 17 Drawing Sheets

(56) References Cited

OTHER PUBLICATIONS

Freiberg et al., "Molecular basis of symbiosis between Rhizobium and legumes," *Nature*, 387:394-401, 1997.
Garg et al., "High-efficiency transformation of Rhizobium leguminosarum by electroporation," *Appl. Env. Microbiol.*, 65:2802-2804, 1999.
GenBank Accession No. AB027257, May 21, 1999.
GenBank Accession No. AF242881, Dec. 22, 2006.
GenBank Accession No. NC_002377, Aug. 17, 2005.
Henderson et al., "The MobA-linked primase is the only replication protein of R1162 required for conjugal mobilization," *J. Bacteriol.*, 181(9):2973-2978, 1999.
Hoekema et al., "A binary plant vector strategy based on separation of vir- and T-region of the Agrobacterium tumefaciens Ti plasmid," *Nature*, 303:179-180, 1983.
Hooykaas et al. "Transfer of the Agrobacterium tumefaciens Ti plasmid to avirulent agrobacteria and to Rhizobium ex planta," *J. Gen. Microbiol.*, 98:477-484, 1977.
Lazo et al., "A DNA transformation-competent *Arabidopsis* genomic library in Agrobacterium," *Bio/Technology*, 9:963-967, 1991.
Pansegrau et al., "Site specific cleavage and joining of single stranded DNA by VirD2 protein of Agrobacterium tumefaciens Ti plasmids; analogy to bacterial conjugation," *Proc. Natl. Acad. Sci. USA*, 90:11538-11542, 1993.
Perez-Mendoza et al., "Identification of functional mob regions in Rhizobium etli: evidence for self-transmissibility of the symbiotic plasmid pRetCFN42d," *J. Bacteriol.*, 186(17):5753-5761, 2004.
Perez-Mendoza, "The relaxase of the rhizobium etli symbiotic plasmid shows nic site cis-acting preference," *J. of Bacteriology*, 188(21):7488-7499, 2006.
Rawlings et al., "Comparative biology of IncQ and IncQ-like plasmids," *Microbiol. Mol. Biol. Rev.*, 65:481-496, 2001.
Shadenkov et al., "VirD2-independent by MobA-dependent transfer of broad-host-range plasmid RSF1010 DNA from Agrobacterium into plant cell nucleus," *Mol. Biol.*, 30:272-275, 1996.
Spaink et al. "Molecular biology of model plant-associated bacteria," In: The Rhizobiaceae, (Eds.), Kluwer Academic Publishers, Dordrecht, The Netherlands, 1998.
Teyssier-Cuvelle et al., "A highly selectable and highly transferable Ti plasmid to study conjugal host range and Ti plasmid dissemination in complex ecosystems," *Microbial Ecology*, 48:10-18, 2004.
Tun-Garrido et al., "Conjugative transfer of p42a from Rhizobium etli CFN42, which is required for mobilization of the symbiotic plasmid, is regulated by quorum sensing," *J. Bacteriol.*, 185(5):1681-1692, 2003.
Turner et al., "Identification and analysis of rhizobial plasmid origins of transfer," *FEMS Microbiol. Ecol.*, 42(2):227-234, 2002.
Van Veen et al., "Ti plasmid containing Rhizobium meliloti are non-tumourogenic on plants, despite proper virulence gene induction and T-strand formation," *Arch. Microbiol.*, 153:85-89, 1989.
Weller et al., "Acquisition of an Agrobacterium Ri plasmid and pathogenicity by other alpha-Proteobacteria in cucumber and tomato crops affected by root mat," *Appl. Environ. Microbiol.*, 70(5):2779-2785, 2004.
Weller et al. "Induction of root-mat symptoms on cucumber plants by *Rhizobium*, but not by *Ochrobactrum* or *Sinorhizobium*, harbouring a cucumopine Ri plasmid," *Pl. Pathol.*, 54(6):799-805, 2005.
Yun et al., "Introduction of ti plasmid into *Bradyrhizobium japonicum* by spheroplast transformation," *Journal of the Korean Agricultural Society*, 30(4):293-299, 1987 (English abstract).
Zhang et al., "The relaxosome protein MobC promotes conjugal plasmid mobilization by extending DNA strand separation to the nick site at the origin of transfer," *Mol. Microbiol.*, 25:509-516, 1997.

* cited by examiner

A) SF4404/pMON96036

B) ML542G/pMON96036

C) SM542C/pMON96036

USE OF NON-*AGROBACTERIUM* BACTERIAL SPECIES FOR PLANT TRANSFORMATION

This application is a continuation of U.S. Ser. No. 14/298,739, filed Jun. 6, 2014, now U.S. Pat. No. 9,365,859; which is a continuation of U.S. Ser. No. 12/975,259, filed Dec. 21, 2010, now abandoned; which is a divisional of U.S. Ser. No. 11/749,583, filed May 16, 2007, issued as U.S. Pat. No. 7,888,552 which claims the priority of U.S. Provisional Patent Application 60/800,872, filed May 16, 2006, the disclosures of which are incorporated by reference in their entirety.

BACKGROUND OF THE INVENTION

1. Field of the Invention

The present invention relates to the field of plant biotechnology. In particular, the invention relates to methods for producing transgenic plants and plant cells by using non-*Agrobacterium* bacterial species.

2. Description of Related Art

*Agrobacterium* spp., members of the Rhizobiales, are common soil bacteria, along with *Rhizobium* spp., *Mesorhizobium* spp., *Sinorhizobium* spp., and related species and genera. A number of wild-type and disarmed (non-pathogenic) strains of *Agrobacterium tumefaciens* and *Agrobacterium rhizogenes* harboring Ti or Ri plasmids can be used for gene transfer into plants. Phytohormone synthesis genes located in the T-DNA of wild type Agrobacteria harboring a Ti or Ri plasmid are expressed in plant cells following transformation, and cause tumor formation or a hairy root phenotype depending on the *Agrobacterium* strain or species. Importantly, T-DNA of Agrobacteria can be engineered to replace many of its virulence and pathogenicity determinants with "genes of interest" while retaining the ability to be transferred into a plant cell and integrated into a plant genome. Strains containing such "disarmed" Ti plasmids are widely used for plant transformation.

The mechanism of T-DNA transfer to plant cells by *Agrobacterium* has been well documented. Briefly, the T-DNA is delimited by two border regions, referred to as right border (RB) and left border (LB). The borders are nicked by virulence protein VirD2 which produces single stranded transferred DNA (the "T-strand") with covalent attachment of the VirD2 on its 5' end. The protein-DNA complex, also including *Agrobacterium* VirE2 protein, exits *Agrobacterium* cells through the so-called Type 4 secretion system (T4SS, both virulence protein and ssDNA transporter), and is transferred into plant cells and integrated in the plant genome with the help of both *Agrobacterium* virulence proteins and plant factors. The use of *Agrobacterium*-mediated vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is efficient in many dicotyledonous plants including *Arabidopsis*, tobacco, and tomato. Methods for *Agrobacterium*-mediated transformation of other species have also been devised (e.g. U.S. Pat. No. 6,384,301, relating to soybean transformation). While *Agrobacterium*-mediated transformation was at first only used with dicotyledonous plants, advances in *Agrobacterium*-mediated transformation techniques made the technique applicable to monocotyledonous plants as well. For example, *Agrobacterium*-mediated transformation techniques have been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and maize (Ishida et al., 1996). However, a number of plant species are recalcitrant to *Agrobacterium*-mediated transformation, and efficiency is low in others. Additionally, since *A. tumefaciens* enters plant tissues at wound sites, and does not naturally infect unwounded tissues, the use of certain tissues as transformation targets is not available.

Besides the T4SS-dependent T-strand delivery system, *Agrobacterium* has additional plasmid mobilization systems that can also transfer and integrate plasmids, such as the IncQ plasmid pRSF1010, between bacterial cells and into the plant genome with lower frequency via conjugal transfer (Buchanan-Wollaston et al. 1987, Shadenkov et al. 1996; Chen et al., 2002). For example, the conjugal transfer protein MobA, in conjunction with MobB and MobC proteins of the RSF1010 plasmid, cleaves the oriT (origin of transfer) site, attaches to the 5' end and transfers the ssDNA into cells independent of the T4SS system (Bravo-Angel et al. 1999 and references therein).

Conjugal transfer systems are widely present in bacteria, resulting in exchange of genetic information between bacterial cells. In *Rhizobium*, phylogenetically related but distinct from *Agrobacterium* (Spaink, et al., (ed.), 1998; Farrand et al., 2003), the conjugal transfer system has been partially characterized in some species (Freiberg et al., 1997: Turner et al. 2002, Tun-Garrido et al. 2003, Perez-Mendoza et al. 2004). The conjugal system requires an oriT as the nicking site and TraA or Mob as a nicking enzyme, which is different from the conventional elements used in T-DNA mobilization (VirD2 and RB and LB sites, respectively). Unlike VirD2, which was found to have plant NLS (nuclear localization signal) at its C-terminus for plant nuclear targeting, the TraA or Mob doesn't have an obvious NLS. The precise mechanism and site of integration of DNA in plants by TraA remains unclear.

Members of the Rhizobiales other than *Agrobacterium* sp., such as *Rhizobium* spp., are known to symbiotically associate with plant roots in specialized nitrogen-fixing nodules (e.g. Long, 2001). In addition to host-specific nodulation of plant roots, especially of legumes, some plant growth promoting effects by members of the Rhizobiales are known in the absence of nodulation (e.g. Noel et al., 1996). Recently, reports have been published describing transformation of plants by bacteria other than *Agrobacterium* sp. (e.g. Broothaerts et al., 2005; U.S. Patent Application Publications 20050289667; 20050289672; Weller et al., 2004; Weller et al, 2005).

Broothaerts et al., reported transformation by *Rhizobium* sp., *Mesorhizobium loti*, and *Sinorhizobium meliloti* strains that was limited to *Arabidopsis*, tobacco, and rice. Weller et al. (2004, 2005) reported that several bacteria, including strains of *Rhizobium* sp. and *Ochrobactrum* sp. that harbored Ri plasmids apparently transformed hydroponically grown cucumber and tomato plants, leading to a hairy root phenotype. However the presence of Agrobacteria was not ruled out as a possibility in some inoculated plants, complicating the analysis. Transfer of DNA to soybean, corn, cotton, or canola plant cells by non-*Agrobacterium* bacterial strains has not been reported. In addition, transformation efforts in rice, tobacco, and *Arabidopsis* with non-*Agrobacterium* bacterial strains have to date been hampered by low transformation efficiencies. There is, therefore, a great need in the art for the development of improved methods allowing the transformation of important crop species using non-*Agrobacterium* bacterial strains, and improving transformation efficiencies in general.

BRIEF DESCRIPTION OF THE FIGURES

The following drawings are part of the present specification and are included to further demonstrate certain aspects of the present invention. The invention may be better understood by reference to the drawings in combination with the detailed description of specific embodiments presented herein.

SUMMARY OF THE INVENTION

Figure 1:
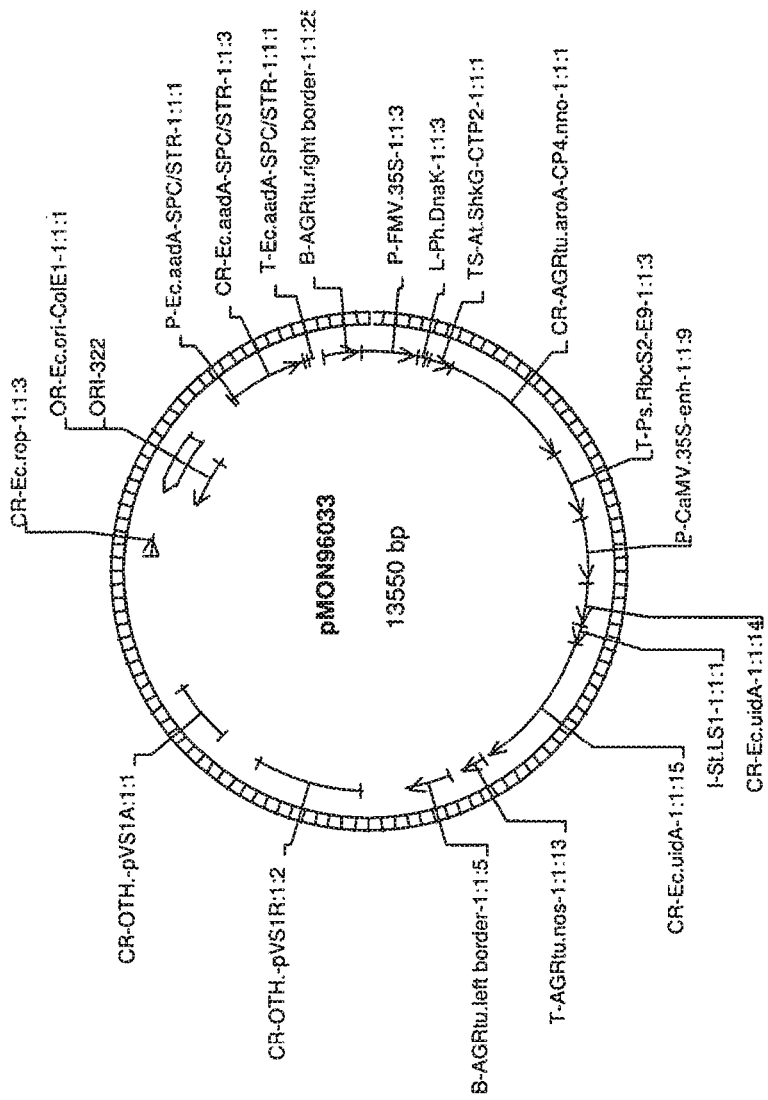
FIG. 1: Schematic map of pMON96033.

In one aspect, the invention provides a method for transforming a plant cell, comprising: (a) contacting at least a first plant cell with a bacterium other than *Agrobacterium* sp. comprising: (i) a first nucleic acid comprising a vir gene region of a Ti plasmid wherein the vir gene region acts to introduce a nucleic acid coding for a sequence of interest into the plant cell in a VirD2-dependent manner; and (ii) a second nucleic acid comprising one or more T-DNA border sequence(s) operably linked to a nucleic acid of interest; and (b) selecting at least a first plant cell transformed with the nucleic acid of interest, wherein the plant cell is a soybean, canola, corn, or cotton plant cell.

In another aspect, the invention provides a method for transforming a plant cell, comprising: (a) contacting at least a first plant cell with a bacterium other than *Agrobacterium* comprising (i) a first nucleic acid required for conjugative transfer of DNA sequences independent of VirD2 function, and (ii) a second nucleic acid comprising a nucleic acid of interest; wherein the plant cell is a soybean, canola, corn, or cotton plant cell and wherein polypeptides encoded by the nucleic acid required for conjugative transfer act to transfer the nucleic acid of interest into the plant cell; and (b) selecting at least a first plant cell transformed with the nucleic acid of interest. In such a method, the conjugative transfer may be traA, traI, or mobA-dependent, and the first nucleic acid comprises oriT. The first nucleic acid may lack left and right T-DNA border sequences.

In a method of the invention, the bacterium may be Rhizobia cell. In certain embodiments, the Rhizobia is grown under suitable conditions to minimize polysaccharide production by the Rhizobia cells. The Rhizobia cell may be grown in the presence of acetosyringone or other compound, such as a phenolic compound, that induces vir gene function prior to contacting the plant cell. The Rhizobia cell may be selected from the group consisting of: *Rhizobium* spp., *Sinorhizobium* spp., *Mesorhizobium* spp., *Phyllobacterium* spp. *Ochrobactrum* spp. and *Bradyrhizobium* spp. In specific embodiments, the Rhizobia cell is a *Rhizobium leguminosarum* cell and may further be a cell of *R. leguminosarum* bv. *trifolii*, *R. leguminosarum* bv. *phaseoli* or *Rhizobium leguminosarum*. bv. *viciae*.

In another aspect of a transformation method provided by the invention, a plant cell that is transformed may be comprised in an explant from a plant seed, for example, from a seedling, callus, cell suspension, cotyledon, meristem, leaf, root, or stem. The explant may comprise an embryonic meristem explant; callus; cell suspension; cotyledon; or tissue from leaves, roots, or stems.

A bacterium used for transformation in accordance with the invention may comprise nucleic acids introduced, for example, by electroporation. The sequences may comprise nucleic acid required for conjugative transfer independent of VirD2 function. The nucleic acids may include first and second nucleic acids.

In another aspect of the invention, a transformation method provided herein may comprise selecting a plant cell transformed with a nucleic acid of interest in the absence of a selection agent. Selecting a plant cell transformed with a nucleic acid of interest may comprise culturing the plant cell in the presence of a selection agent, wherein the nucleic acid of interest confers tolerance to the selection agent or is operably linked to a further nucleic acid that confers tolerance to the selection agent. Examples of such selection agents include glyphosate, kanamycin, bialaphos or dicamba. In one embodiment, the nucleic acid of interest or further nucleic acid encodes EPSP synthase and in a still further embodiment encodes the EPSP synthase protein CP4. In another embodiment, the selection agent is glyphosate. In yet other embodiments, the sequence of interest may be defined as not physically linked to a selectable marker gene. For example, the marker gene and nucleic acid of interest may genetically segregate in progeny of a plant regenerated from the plant cell transformed with the nucleic acid of interest.

A bacterium in accordance with the invention may comprise at least a third nucleic acid comprising a further nucleic acid of interest, wherein the plant cell is transformed with the third nucleic acid. In a method of the invention, a plant may be regenerated a transgenic plant cell, wherein the plant comprises the sequence of interest. Regenerating a plant may comprise inducing formation of one or more shoots from an explant comprising the plant cell and cultivating at least a first shoot into a whole fertile plant. In certain embodiments, the plant may be a corn or cotton plant. In further embodiments, regeneration occurs by organogenesis. In other embodiments, the plant is a soybean or canola plant.

In another aspect, the invention provides a Rhizobia cell selected from the group consisting of: *Rhizobium* spp., *Sinorhizobium* spp., *Mesorhizobium* spp., *Phyllobacterium* spp. *Ochrobactrum* spp. and *Bradyrhizobium* spp., the cell comprising (i) a first nucleic acid comprising a vir gene region of a Ti plasmid wherein the vir gene region acts to introduce a nucleic acid coding for a sequence of interest into a plant cell in a VirD2-dependent manner: and (ii) a second nucleic acid comprising one or more T-DNA border sequence(s) operably linked to a nucleic acid coding for a sequence of interest. In one embodiment, the cell is further defined as comprising a selectable marker. In another embodiment, the Rhizobia cell is selected from the group consisting of: *Rhizobium* sp., *Rhizobium* sp. NGR234, *Rhizobium leguminosarum* Madison, *R. leguminosarum* USDA2370, *R. leguminosarum* USDA2408, *R. leguminosarum* USDA2668, *R. leguminosarum* 2370G, *R. leguminosarum* 2370LBA, *R. leguminosarum* 2048G, *R. leguminosarum* 2048LBA, *R. leguminosarum* bv. *phaseoli*, *R. leguminosarum* bv. *phaseoli* 2668G, *R. leguminosarum* bv. *phaseoli* 2668LBA, *R. leguminosarum* RL542C, *R. leguminosarum* bv. *viciae*, *R. leguminosarum* bv. *trifolii*, *Rhizobium etli* USDA 9032, *R. etli* bv. *phaseoli*, *Rhizobium tropici*, *Mesorhizobium* sp., *Mesorhizobium loti* ML542G, *M. loti* ML4404, *Sinorhizobium* sp., *Sinorhizobium meliloti* SD630, *S. meliloti* USDA 1002, *Sinorhizobium fredii* USDA205, *S. fredii* SF542G, *S. fredii* SF4404, *S. fredii* SM542C, *Bradyrhizobium* sp., *Bradyrhizobium japonicum* USDA 6, and *B. japonicum* USDA 110. In specific embodiments, the cell is a *Rhizobium leguminosarum* cell and may further be. For example, a *R. leguminosarum* bv. *trifolii*, *R. leguminosarum* bv. *phaseoli* or *Rhizobium leguminosarum*. bv. *viciae* cell.

In yet another aspect of the invention, a DNA construct is provided competent for virD2-independent transfer from Rhizobia and lacking T-DNA border sequence, the construct comprising an oriT sequence and traA or mob sequence operably linked to a nucleic acid of interest. The invention further provides a Rhizobia cell transformed with such a DNA construct of claim 35, wherein the Rhizobia is selected from the group consisting of: *Rhizobium* spp., *Sinorhizobium* spp., *Mesorhizobium* spp., *Phyllobacterium* spp. *Ochrobactrum* spp. and *Bradyrhizobium* spp. In one embodiment, the Rhizobia cell is selected from the group consisting of: *Rhizobium* sp., *Rhizobium* sp. NGR234, *Rhizobium leguminosarum* Madison, *R. leguminosarum* USDA2370, *R. leguminosarum* USDA2408, *R. leguminosarum* USDA2668, *R. leguminosarum* 2370G, *R. leguminosarum* 2370LBA, *R. leguminosarum* 2048G, *R. leguminosarum* 2048LBA, *R. leguminosarum* bv. *phaseoli*. *R. leguminosarum* bv. *phaseoli* 2668G, *R. leguminosarum* bv. *phaseoli* 2668LBA, *R. leguminosarum* RL542C, *R. leguminosarum* bv. *viciae*, *R. leguminosarum* bv. *trifolii*, *Rhizobium etli* USDA 9032, *R. etli* bv. *phaseoli*, *Rhizobium* 15 *tropici*, *Mesorhizobium* sp., *Mesorhizobium loti* ML542G, *M. loti* ML4404, *Sinorhizobium* sp., *Sinorhizobium meliloti* SD630, *S. meliloti* USDA1002. *Sinorhizobium fredii* USDA205, *S. fredii* SF542G, *S. fredii* SF4404, *S. fredii* SM542C, *Bradyrhizobium* sp., *Bradyrhizobium japonicum* USDA 6, and *B. japonicum* USDA 110. In specific embodiments, the cell is a *Rhizobium leguminosarum* cell, and in still further embodiments, may be a *R. leguminosarum* bv. *trifolii*, *R. leguminosarum* bv. *phaseoli* or *Rhizobium leguminosarum*. bv. *viciae* cell.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The present invention provides methods and compositions for the efficient genetic transformation of plant cells of important crop species by Rhizobia. The invention overcomes substantial limitations in the art, including limited transformation efficiency and failure to describe techniques amenable to transformation of important crop plants by use of non-Agrobacterial strains. For example, while use of bacteria other than *Agrobacterium* has been discussed for several plant varieties, transformation frequencies have been low. In the case of rice, transformation frequencies of 0.6% and lower have been reported, with only one transformed plant obtained from 687 inoculated calli (Broothaerts et al., 2005). This contrasts to 50-80% transformation frequencies using *Agrobacterium*. Even using model organisms easily transformed by *Agrobacterium*, transformation frequencies were only a fraction of those obtained by *Agrobacterium*-mediated transformation.

To date considerable research had been required in many instances to apply even well developed transformation procedures such as *Agrobacterium*-mediated transformation to different plant species. Plants of different species often exhibit substantial physiological differences that effect amenability to genetic transformation. Methods for transformation of one species of plant therefore often do not work effectively, if at all, with other plants and the ability to transform a plant is not necessarily predictive of the ability to transform even related species using that procedure. This is particularly true for bacterial transformation, which involves complex biochemical interactions between the bacterial strains used and target plant cells. Rhizobia interact with plants in the native environment and therefore can exhibit host-specificities, the impact of which is unknown for many crop species.

Figure 4:
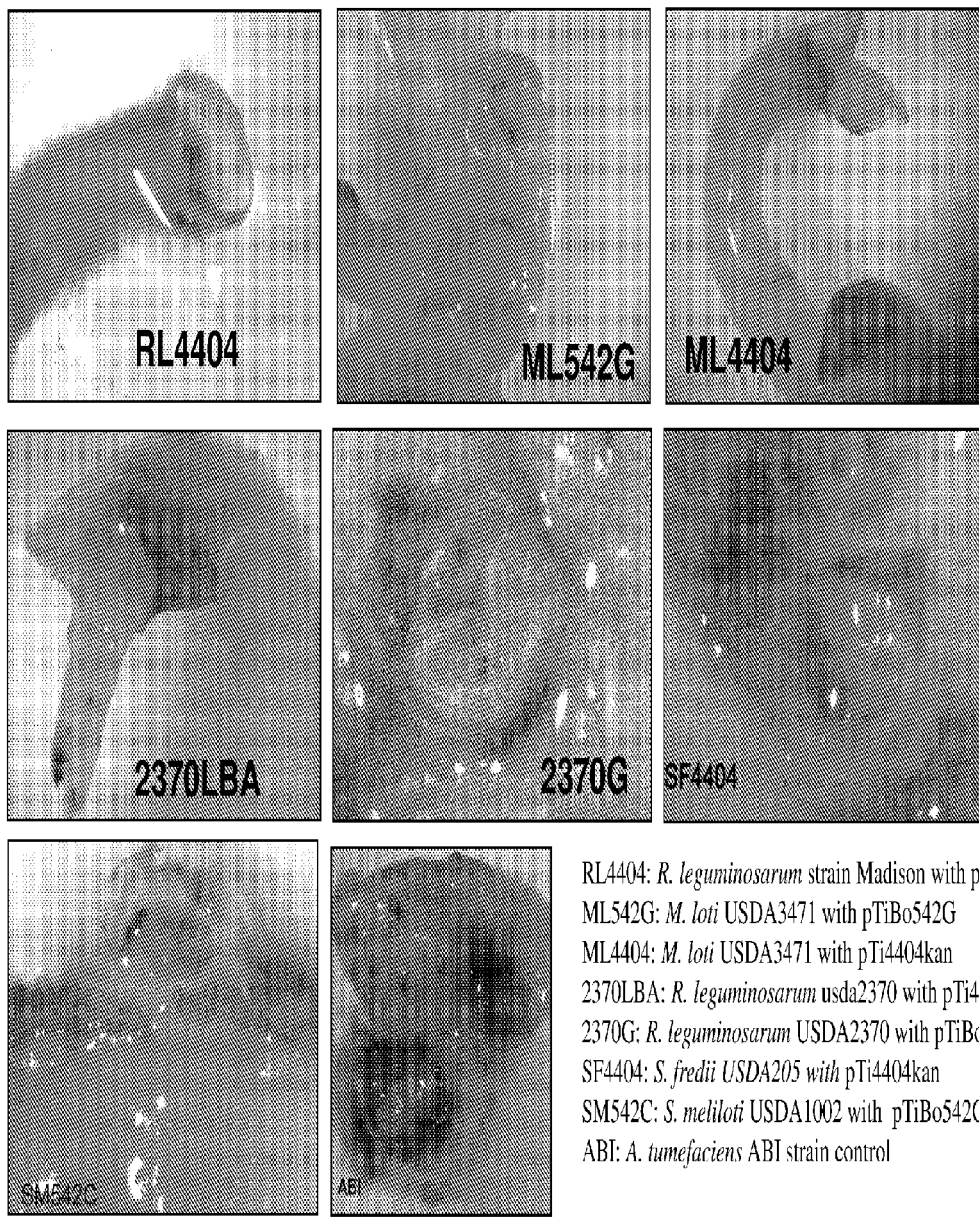
FIG. 4: Transient GUS assay of *Rhizobium*-mediated transformation in soybean with *Mesorhizobium loti* (ML), *Rhizobium leguminosarum* (RL), *Sinorhizobium fredii* (SF), *Sinorhizobium meliloti* (SM) with either disarmed Ti-plasmid (pTiBo542G or pTi4404kan). RL4404: *R. leguminosarum* strain Madison with pTi4404kan; ML542G: *M. loti* USDA3471 with pTiBo542G; ML4404: *M. loti* USDA3471 with pTi4404kan; 2370LBA: *R. leguminosarum* USDA2370 with pTi4404kan; 2370G: *R. leguminosarum* USDA2370 with pTiBo542G; SF4404: *S. fredii* USDA205 with pTi4404kan; SM542C: *S. meliloti* USDA1002 with pTiBo542G; ABI: *A. tumefaciens* ABI strain control.

Thus, identifying plants amenable to Rhizobia-mediated transformation, and developing procedures allowing increased transformation efficiencies is of great interest. Efficient transformation in particular is important because the extent to which any given transformation event is expressed can vary substantially depending upon the integration site in the plant genome. The ability to select transformation events having a suitable expression profile is thus dependent upon the ability to efficiently produce transformants. As explained in the working examples below, transient transformation frequencies of as high as 5% were obtained by the inventors for the transformation of soybeans (FIG. 4) and frequencies approaching 56% and 33% were obtained in the case of cotton (FIG. 12) and canola (FIG. 9), respectively.

The present invention overcomes limitations in the art by providing, in one embodiment, techniques for the use of Rhizobia to transform important crop plants that were not previously known to be transformable by Rhizobia, including canola, corn, cotton, and soybean. The invention also provides techniques for the efficient transformation of plants using Rhizobia, including those already known to be amenable to transformation by Rhizobia at a low frequency. The invention also provides methods for the transformation of tissue targets differing from those of *Agrobacterium*. For example, while *Agrobacterium* typically requires a wound site to infect plants, some other members of the Rhizobiales, including Rhizobiaceae such as *Rhizobium*, naturally infect plant roots via infection threads that penetrate plant tissues, allowing for use of non-wounded tissue as a transformation target.

The following definitions are provided in order to aid those skilled in the art in understanding the detailed description of the present invention.

As used herein, "plant growth regulator" or "plant hormone" refers to compounds that affect plant growth. Plant growth regulators include, but are not limited to, auxins, cytokinins, ABA, gibberellins, ethylene, brassinosteroids, and polyamines. Auxins affect the elongation of shoots and roots at low concentration but inhibit growth at higher levels. Commonly used auxins include picloram (4-amino-3,5,6-trichloropicolinic acid), 2,4-D (2,4-dichlorophenoxyacetic acid), IAA (indole-3-acetic acid), NAA ($\alpha$-naphthaleneacetic acid), and dicamba (3,6-dichloroanisic acid). Cytokinins cause cell division, cell differentiation, and shoot differentiation. Commonly used cytokinins include kinetin, BA (6-benzylaminopurine), 2-ip (2-isopentenyladenine), BAP (6-benzylaminopurine), thidiazuron (TDZ), zeatin riboside, and zeatin.

"Coding sequence", "coding region" or "open reading frame" refers to a region of continuous sequential nucleic acid triplets encoding a protein, polypeptide, or peptide sequence.

"Dicot" or "dicotyledonous" refers to plants having two cotyledons. Examples include, without limitation, plants such as alfalfa, beans, broccoli, cabbage, canola, carrot, cauliflower, celery, cotton, cucumber, eggplant, lettuce, melon, pea, pepper, potato, pumpkin, radish, rapeseed, spinach, soybean, squash, tomato, and watermelon.

"Endogenous" refers to materials originating from within the organism or cell.

"Exogenous" refers to materials originating from outside of the organism or cell. As used herein, exogenous is intended to refer to any nucleic acid from a source other than the recipient cell or tissue, regardless of whether a similar (but not identical) nucleic acid may already be present in the recipient cell or tissue.

"Explant" refers to a plant part that is capable of being transformed and subsequently regenerated into a transgenic plant. Examples include embryos, callus, cell suspensions, cotyledons, meristems, seedlings, seeds, leaves, stems or roots.

"Monocot" or "monocotyledonous" refers to plants having a single cotyledon. Examples include, without limitation, onions, corn, rice, sorghum, wheat, rye, millet, sugarcane, oat, triticale, barley and turfgrass.

"Nucleic acid" refers to deoxyribonucleic acid (DNA) or ribonucleic acid (RNA).

"Phenotype" refers to a trait exhibited by an organism resulting from the expression (or lack of expression) of nucleic acids in the genome (including non-genomic DNA and RNA such as plasmids and artificial chromosomes) and/or organelles of the organism.

The term "plant" encompasses any higher plant and progeny thereof, including monocots (e.g., corn, rice, wheat, barley, etc.), dicots (e.g., soybean, cotton, tomato, potato, *Arabidopsis*, tobacco, etc.), gymnosperms (pines, firs, cedars, etc) and includes parts of plants, including reproductive units of a plant (e.g., seeds, bulbs, tubers, meristematic tissues, or other parts or tissues from that the plant can be reproduced), fruits and flowers.

"Polyadenylation signal" or "polyA signal" refers to a nucleic acid sequence located 3' to a coding region that promotes the addition of adenylate nucleotides to the 3' end of an mRNA transcribed from the coding region.

"Promoter" or "promoter region" refers to a nucleic acid sequence, usually found 5' to a coding sequence, that alters expression of the coding sequence by providing a recognition site for RNA polymerase and/or other recognition sites for other transcription-related factors utilized to produce RNA and/or initiate transcription at the correct site on the DNA.

"Recombinant nucleic acid vector" or "vector" or "construct" refers to any agent such as a plasmid, cosmid, virus, autonomously replicating sequence, phage, or linear or circular single- or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid vectors or constructs typically comprise a 5' regulatory sequence or promoter region and a coding sequence encoding for a desired gene product. The vectors are typically designed such that once delivered into a cell or tissue, the coding sequence is transcribed into mRNA, which is optionally translated into a polypeptide or protein.

"Regeneration" refers to the process of growing a plant from a plant cell or tissue.

"Rhizobia" refers without limitation to bacterial genera, species, and strains that may be assigned to the order Rhizobiales other than *Agrobacterium* bacterial strains comprising the taxonomic families Rhizobiaceae (e.g. *Rhizobium* spp., *Sinorhizobium* spp.); Phyllobacteriaceae (e.g. *Mesorhizobium* spp., *Phyllobacterium* spp.); Brucellaceae (e.g. *Ochrobactrum* spp.); Bradyrhizobiaceae (e.g. *Bradyrhizobium* spp.), and Xanthobacteraceae (e.g. *Azorhizobium* spp.), among others. For the purposes of the present application, "Rhizobia" does not include, biovars, or species.

Taxonomic assignment may be done as is known in the art, for instance by comparison of 16S rDNA sequences or other classification methods. Wild type strains of many *Rhizobium* species are typically able to induce formation of nitrogen fixing nodules in root tissues of host plants such as leguminous plants (Fabaceae). However, the ability to nodulate roots of a given plant species is not required for *Rhizobium*-mediated DNA transfer into cells of the plant species.

"Selectable marker" or "screenable marker" refers to a nucleic acid sequence whose expression confers a phenotype facilitating identification of cells, tissues, or plants containing the nucleic acid sequence.

"Transcription" refers to the process of producing an RNA copy from a DNA template.

"Transformation" refers to a process of introducing an exogenous nucleic acid sequence into a cell or tissue. The transformation may be transient or stable. In stable transformations, part or all of the exogenous nucleic acid is incorporated (e.g., integrated or stably maintained) in the nuclear genomic DNA, plastid DNA, or is capable of autonomous replication in the nucleus or plastid.

"Transgenic" refers to organisms into which an exogenous nucleic acid sequence has been stably transformed.

In designing a vector for the transformation process, one or more genetic components are selected that will be introduced into the plant cell or tissue. Genetic components can include any nucleic acid that is introduced into a plant cell or tissue using the method according to the invention. Genetic components can include non-plant DNA, plant DNA or synthetic DNA.

In one embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and to regulate expression of the structural nucleic acid sequence. In one preferred embodiment, the genetic components are oriented so as to express a mRNA, that in an optional embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of any DNA construct in plant cells, including, for instance, promoters regulated by (1) heat (Callis et al., 1988, (2) light (e.g., pea RbcS-3A promoter, Kuhlemeier et al., (1989); maize RbcS promoter, Schaffner et al., (1991); (3) hormones, such as abscisic acid (Marcotte et al., 1989, (4) wounding (e.g., Wuni, Siebertz et al., 1989); or other signals or chemicals. Tissue specific expression is also known. As described below, it is preferred that the particular promoter selected should be capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter, OsAct1), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. Pat. No. 7,151,204 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987; U.S. Pat. Nos. 6,051,753; 5,378,619), the sucrose synthase promoter (Yang et al., 1990), the R gene complex promoter (Chandler et al., 1989), and the chlorophyll a/b binding protein gene promoter, PC1SV (U.S. Pat. No. 5,850,019). In the present invention, CaMV35S with enhancer sequences (e35S; U.S. Pat. Nos. 5,322,938; 5,352,605; 5,359,142; and 5,530,196), FMV35S (U.S. Pat. Nos. 6,051,753; 5,378,619), peanut chlorotic streak caulimovirus (PC1SV; U.S. Pat. No. 5,850,019), At.Act 7 (Accession #U27811). At.ANT1 (U.S. Patent Application 20060236420), FMV.35S-EF1a (U.S. Patent Application Publication 2005/0022261), eIF4A10 (Accession #X79008) and AGRtu.nos (GenBank Accession V00087; Depicker et al, 1982; Bevan et al., 1983), rice cytosolic triose phosphate isomerase (OsTPI; U.S. Pat. No. 7,132,528), and rice actin 15 gene (OsAct15; U.S. Patent Application Publication 2006/0162010 promoters may be of particular benefit. In some instances, e.g. OsTPI and OsAct 15, a promoter may include a 5'UTR and/or a first intron.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

The promoters used in the DNA constructs (i.e. chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase or decrease translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat. No. 5,362,865). Examples of non-translation leader sequences include maize and petunia heat shock protein leaders (U.S. Pat. No. 5,362,865), plant virus coat protein leaders, plant rubisco leaders. GmHsp (U.S. Pat. No. 5,659,122). PhDnaK (U.S. Pat. No. 5,362,865), AtAnt1, TEV (Carrington and Freed, 1990), OsAct1 (U.S. Pat. No. 5,641,876), OsTPI (U.S. Pat. No. 7,132,528), and OsAct15 (U.S. Publication No. 20060162010), and AGRtu.nos (GenBank Accession V00087; Bevan et al., 1983). Other genetic components that serve to enhance expression or affect transcription or translational of a gene are also envisioned as genetic components.

Intron sequences are known in the art to aid in the expression of transgenes in monocot plant cells. Examples of introns include the corn actin intron (U.S. Pat. No. 5,641,876), the corn HSP70 intron (ZmHSP70; U.S. Pat. No. 5,859,347; U.S. Pat. No. 5,424,412), and rice TPI intron (OsTPI; U.S. Pat. No. 7,132,528) and are of benefit in practicing this invention.

Termination of transcription may be accomplished by a 3' non-translated DNA sequence operably linked to a recombinant transgene (e.g. the gene of interest, the identification sequence comprising a screenable gene, or the plant selectable marker gene). The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region (Fraley et al., 1983), is commonly used in this capacity. Polyadenylation molecules from a *Pisum sativum* RbcS2 gene (Ps.RbcS2-E9; Coruzzi et al., 1984), AGRtu.nos (Genbank Accession E01312), E6 (Accession #U30508), rice glutelin (Okita et al., 1989), and TaHsp17 (wheat low molecular weight heat shock protein gene; GenBank Accession #X13431) in particular may be of benefit for use with the invention.

In one embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection or screening device may function in a regenerable plant tissue to produce a compound that would confer upon the plant tissue resistance to an otherwise toxic compound. A number of screenable or selectable marker genes are known in the art and can be used in the present invention. Examples of selectable markers and genes providing resistance against them are disclosed in Miki and McHugh, 2004. Genes of interest for use as a selectable, screenable, or scoreable marker would include but are not limited to gus, gfp (green fluorescent protein), luciferase (LUX), genes conferring tolerance to antibiotics like kanamycin (Dekeyser et al., 1989), neomycin, kanamycin, paromomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase, genes that encode enzymes that give tolerance to herbicides like glyphosate (e.g. 5-enolpyruvylshikimate-3-phosphate synthase (EPSPS): Della-Cioppa et al., 1987; U.S. Pat. No. 5,627,061; U.S. Pat. No. 5,633,435; U.S. Pat. No. 6,040,497; U.S. Pat. No. 5,094,945; WO04074443, and WO04009761; glyphosate oxidoreductase (GOX; U.S. Pat. No. 5,463,175): glyphosate decarboxylase (WO05003362 and US Patent Application 20040177399; or glyphosate N-acetyltransferase (GAT): Castle et al., U.S. Patent Publication 20030083480), dalapon (e.g. dehI encoding 2,2-dichloropropionic acid dehalogenase conferring tolerance to 2,2-dichloropropionic acid (Dalapon; WO9927116)), bromoxynil (haloarylnitrilase (Bxn) for conferring tolerance to bromoxynil (WO8704181A1; U.S. Pat. No. 4,810,648; WO8900193A)), sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. No. 6,225,105; U.S. Pat. No. 5,767,366, U.S. Pat. No. 4,761,373; U.S. Pat. No. 5,633,437; U.S. Pat. No. 6,613,963; U.S. Pat. No. 5,013,659; U.S. Pat. No. 5,141,870; U.S. Pat. No. 5,378,824; U.S. Pat. No. 5,605,011)); encoding ALS, GST-II), bialaphos or phosphinothricin or derivatives (e.g. phosphinothricin acetyltransferase (bar) conferring tolerance to phosphinothricin or glufosinate (U.S. Pat. No. 5,646,024, U.S. Pat. No. 5,561,236, EP 275,957; U.S. Pat. No. 5,276,268; U.S. Pat. No. 5,637,489: U.S. Pat. No. 5,273,894), atrazine (encoding GST-III), dicamba (dicamba monooxygenase (DMO); US Patent Applications 20030115626, 20030135879), or sethoxydim (modified acetyl-coenzyme A carboxylase for conferring tolerance to cyclohexanedione (sethoxydim) and aryloxyphenoxypropionate (haloxyfop) (U.S. Pat. No. 6,414,222)), among others. Other selection procedures can also be implemented including positive selection mechanisms (e.g. use of the manA gene of *E. coli*, allowing growth in the presence of mannose) and would still fall within the scope of the present invention (see also Miki and McHugh (2004)).

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. Nos. RE37,543; 6,228,623; 5,958,745 and U.S. Patent Publication No. US20030028917). Also environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the DNA sequences of interest can affect these phenotypes by the inhibition of expression of an endogenous gene via gene silencing technologies such as cosuppression, antisense, RNAi, expression of miRNAs (natural or engineered), expression of trans-acting siRNAs, and expression of ribozymes (see e.g., U.S. Patent Application Publication 20060200878).

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

For Rhizobia-mediated transformation, after the construction of the plant transformation vector or construct, the nucleic acid molecule, prepared as a DNA composition in vitro, is introduced into a suitable host such as *E. coli* and mated into another suitable host such as Rhizobia, including *Rhizobium*, or directly transformed (e.g. electroporated) into competent Rhizobia. The Ti or Ri plasmid may be naturally transferred into nitrogen-fixing *Rhizobium* and may induce tumors or hairy roots, respectively (Hooykaas et al. 1977, Weller et al. 2004). Such Ti or Ri plasmid may alternatively be "disarmed", and unable to cause plant cell proliferation. Since *Rhizobium* and *Agrobacterium* have differing infection mechanisms, deep infection by *Rhizobium* or other Rhizobia through its infection thread may increase the frequency of germ line transformation of a gene of interest during soybean transformation once the Ti or Ri helper plasmid is introduced.

The present invention encompasses the use of bacterial strains to introduce one or more genetic components into plants. In one embodiment, the hosts contain disarmed Ti or Ri plasmids that do not contain the oncogenes that cause tumorigenesis or rhizogenesis, derivatives of which are used as the vectors and contain the genes of interest that are subsequently introduced into plants. In another embodiment, the bacteria transfer DNA into plant cells by means of a T4SS-independent mechanism, namely oriT-mediated conjugal transfer. Functions needed for T4SS-independent DNA transfer may reside on the plasmid containing the DNA to be transferred, or may reside on the chromosome or another plasmid, including a Ti or Ri plasmid, also present in such a bacterial cell.

Bacterial species and strains include but are not limited to *Rhizobium* sp., *Rhizobium* sp. NGR234, *Rhizobium leguminosarum* Madison, *R. leguminosarum* USDA2370, *R. leguminosarum* USDA2408, *R. leguminosarum* USDA2668, *R. leguminosarum* 2370G, *R. leguminosarum* 2370LBA, *R. leguminosarum* 2048G, *R. leguminosarum* 2048LBA, *R. leguminosarum* bv. *phaseoli*. *R. leguminosarum* bv. *phaseoli* 2668G, *R. leguminosarum* bv. *phaseoli* 2668LBA, *R. leguminosarum* RL542C, *R. leguminosarum* bv. *viciae*. *R. leguminosarum* bv. *trifolii*, *Rhizobium etli* USDA 9032, *R. etli* bv *phaseoli*, *Rhizobium tropici*, *Mesorhizobium* sp., *Mesorhizobium loti* ML542G, *M. loti* ML4404, *Sinorhizobium* sp., *Sinorhizobium meliloti* SD630, *S. meliloti* USDA 1002, *Sinorhizobium fredii* USDA205, *S. fredii* SF542G, *S. fredii* SF4404, *S. fredii* SM542C, *Bradyrhizobium* sp., *Bradyrhizobium japonicum* USDA 6, *B. japonicum* USDA 110.

Any suitable plant culture medium can be used to develop or maintain a plant tissue culture, supplemented as appropriate with additional plant growth regulators including but not limited to auxins such as picloram (4-amino-3,5,6-trichloropicolinic acid), 2,4-D (2,4-dichlorophenoxyacetic acid) and dicamba (3,6-dichloroanisic acid); cytokinins such as BAP (6-benzylaminopurine) and kinetin; ABA: and gibberellins. Other media additives can include but are not limited to amino acids, macro elements, iron, microelements, inositol, vitamins and organics, carbohydrates, undefined media components such as casein hydrolysates, with or without an appropriate gelling agent such as a form of agar, such as a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (1962), N6 (Chu et al., 1975), Linsmaier and Skoog (1965), Uchimiya and Murashige (1962), Gamborg's media (Gamborg et al., 1968), D medium (Duncan et al., 1985), McCown's Woody plant media (McCown and Lloyd, 1981), Nitsch and Nitsch (1969), and Schenk and Hildebrandt (1972) or derivations of these media supplemented accordingly. Those of skill in the art are aware that media and media supplements such as nutrients and growth regulators for use in transformation and regeneration and other culture conditions such as light intensity during incubation, pH, and incubation temperatures that can be optimized for the particular variety of interest.

After a transformable plant tissue is isolated or developed in tissue culture, or transformable plant tissue is identified and/or prepared in planta, the next step of the method is introducing the genetic components into the plant tissue. This process is also referred to herein as "transformation." The plant cells are transformed and optionally subject to a selection step. The independent transformants are referred to as transgenic events. A number of methods utilizing *Agrobacterium* strains have been reported and can be used to insert genetic components into transformable plant tissue. However, non-*Agrobacterium* spp. had not typically been utilized to transform plants.

Those of skill in the art are aware of the typical steps in the plant transformation process. The Rhizobia to be used can be prepared either by inoculating a liquid medium such as TY or YEM media (Beringer et al., 1974) directly from a glycerol stock or streaking the bacteria onto a solidified media from a glycerol stock, allowing the bacteria to grow under the appropriate selective conditions. The Rhizobia may be "pre-induced" by growth under nutritional or cultural conditions including the presence of acetosyringone in an amount that facilitates transformation. Those of skill in the art are familiar with procedures for growth and suitable culture conditions for bacteria as well as subsequent inoculation procedures. The density of the bacterial culture used for inoculation and the ratio of the number of bacterial cells to amount of explant tissue can vary from one system to the next, and therefore optimization of these parameters for any transformation method is expected.

The next stage of the transformation process is the inoculation. In this stage the suitably prepared plants, plant tissues, or explants, and the bacterial cell suspension are mixed together. The duration and condition of the inoculation and bacterial cell density will vary depending on the plant transformation system. Growth or inoculation of transforming bacteria may occur in the presence of acetosyringone, or other known inducer of expression of the virulence genes located on Ti or Ri plasmids. In certain embodiments, growing of the bacterium other than *Agrobacterium* sp. is done under conditions to minimize polysaccharide production during growth in induction medium. In particular embodiments, the carbon source used to minimize polysaccharide production during Rhizobia growth in induction medium is glucose in AB-TY medium, or L-arabinose and potassium gluconate in ATA medium.

After inoculation any excess bacterial suspension can be removed and the bacteria and target plant material are co-cultured. The co-culture refers to the time post-inoculation and prior to transfer to an optional delay or selection medium. Any number of plant tissue culture media can be used for the co-culture step. Plant tissues after inoculation with bacteria may be cultured in a liquid or semi-solid media. The co-culture is typically performed for about one to four days.

After co-culture with bacteria, the inoculated plant tissues or explants can optionally be placed directly onto selective media. Alternatively, after co-culture with bacteria, they could be placed on media without the selective agent and subsequently placed onto selective media. Those of skill in the art are aware of the numerous modifications in selective regimes, media, and growth conditions that can be varied depending on the plant system and the selective agent. Typical selective agents include but are not limited to antibiotics such as geneticin (G418), kanamycin and paromomycin, or the herbicides glyphosate, glufosinate, and DICAMBA. Additional appropriate media components can be added to the selection or delay medium to inhibit bacterial growth. Such media components can include, but are not limited to, antibiotics such as carbenicillin or cefotaxime.

The cultures are subsequently transferred to a medium suitable for the recovery of transformed plantlets. Those of skill in the art are aware of the number of methods to recover transformed plants. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

Once the transformable plant tissue is inoculated, plant cells in the tissue may be transformed, and independently transformed plant cells are selected. The independent transformants are referred to as transgenic events. *Agrobacterium*-mediated transformation and regeneration systems for many monocot and dicot plant species are known in the art (e.g. Komari et al., 1998: Zhou et al. 1995; Hiei et al., 1994. Plant J.; 6:271-282; Ishida et al. 1996; Rogers et al., 1987; Schrammeijer et al., 1990; U.S. Pat. No. 6,384,301), although use of Rhizobia for plant cell transformation has been reported only for tobacco, *Arabidopsis*, and rice (Broothaerts et al., 2005). Following transformation and regeneration, transgenic plants are identified. Finally, one of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

The transformants produced, and their progeny, may subsequently be analyzed to determine the presence or absence of a particular nucleic acid of interest contained on the transformation vector. Molecular analyses can include but are not limited to Southern blots (Southern, 1975), PCR (polymerase chain reaction) analyses, analysis of enzymatic activities, immunodiagnostic approaches, and field evaluations and the like (Also see, for example. Sambrook et al., 1989). These and other well known methods can be performed to confirm the stability of the transformed plants produced by the methods disclosed.

The above-described techniques may be suitable for any plant and is especially useful for plants such as alfalfa, barley, beans, beet, broccoli, cabbage, carrot, canola, cauliflower, celery, Chinese cabbage, corn, cotton, cucumber, dry bean, eggplant, fennel, garden beans, gourd, leek, lettuce, melon, oat, okra, onion, pea, pepper, pumpkin, peanut, potato, pumpkin, radish, rice, sorghum, soybean, spinach, squash, sweet corn, sugarbeet, sunflower, tomato, watermelon, and wheat.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Rhizobium and Agrobacterium Strains

Agrobacterium tumefaciens AGL0 was obtained from ATCC (ATCC Number: BAA-100™, Lazo et al., 1991). Rhizobium leguminosarum strain Madison and Sinorhizobium meliloti SD630 were isolated from weed clover in a home garden in Madison, Wis., USA, and confirmed by sequencing the PCR product of a 16S rRNA amplified with the following primers: 5' GAGAGTTTGATCCTG-GCTCAG 3' (Xd578; SEQ ID NO:1) and 5' AAGGAGGT-GATCCAGCCGCAG 3' (Xd579; SEQ ID NO:2). Other Rhizobium strains were obtained from USDA Rhizobium collection center (Table 1). Rhizobium strains were grown in TY or MAG medium and Agrobacterium in LB medium. Strains are shown below and 16s rRNA sequences amplified in strains isolated are provided as SEQ ID NOs:24-30.

TABLE 1

Agrobacterium and Rhizobium strains

| Strain Name | Ti plasmid | Source |
|---|---|---|
| A. tumefaciens AGL0 | pTiBo542 | ATCC; Lazo et al., 1991 |
| A. tumefaciens LBA4404 | pAL4404 | Hoekema et al., 1983 |
| A. tumefaciens AGL0C | pTiBo542C (kanR) | This study |
| A. tumefaciens AGL0G | pTiBo542G (kanR) | This study |
| A. tumefaciens 4404TIK | pTi4404kan (kanR) | This study |
| A. tumefaciens ABI | pTiC58 (kanR, gentR) | Monsanto |

TABLE 1-continued

Agrobacterium and Rhizobium strains

| Strain Name | Ti plasmid | Source |
|---|---|---|
| Rhizobium leguminosarum Madison | None | This study |
| Sinorhizobium meliloti SD630 | None | This study |
| Rhizobium leguminosarum USDA2370 | None | USDA Rhizobium collection center |
| Rhizobium leguminosarum bv. trifolii USDA2048 | None | USDA Rhizobium collection center |
| Rhizobium leguminosarum bv. phaseoli USDA2668 | None | USDA Rhizobium collection center |
| Sinorhizobium fredii USDA205 | None | USDA Rhizobium collection center |
| Sinorhizobium meliloti USDA1002 | None | USDA Rhizobium collection center |
| Mesorhizobium loti USDA 3471 | None | USDA Rhizobium collection center |
| Bradyrhizobium japonicum USDA 6 | None | USDA Rhizobium collection center |
| Bradyrhizobium japonicum USDA 110 | None | USDA Rhizobium collection center |
| Rhizobium etli USDA 9032 (CFN42) | None | USDA Rhizobium collection center |
| R. leguminosarum 2370G | pTiBo542G | This study |
| R. leguminosarum 2370LBA | pTi4404kan | This study |
| R. leguminosarum bv. trifolii 2048G | pTiBo542G | This study |
| R. leguminosarum bv. trifolii 2048LBA | pTi4404kan | This study |
| R. leguminosarum bv. phaseoli 2668G | pTiBo542G | This study |
| R. leguminosarum bv. phaseoli 2668LBA | pTi4404kan | This study |
| R. leguminosarum RL542C | pTiBo542C | This study |
| S. fredii SF542G | pTiBo542G | This study |
| S. fredii SF4404 | pTi4404kan | This study |
| S. meliloti SM542C | pTiBo542C | This study |
| M. loti ML542G | pTiBo542G | This study |
| M. loti ML4404 | pTi4404kan | This study |

Example 2

Transformation of Agrobacterium

The Agrobacterium competent cells were prepared by washing a log phase culture in LB medium with chilled deionized water and 10% glycerol, and stored at −80° C. Fifty microliters of thawed competent cells were mixed with 1 or 2 µl DNA on ice and electroporated in 1 mm gap curvet with 200 ohm resistance, 25 µF capacity and 1.8 kv using a BIO-RAD Gene Pulser® II device (BIO-RAD, Hercules, Calif.).

Example 3

Construction of Ti Plasmids with an Antibiotic Selectable Marker Gene

To select Ti plasmids in Rhizobium spp., a homologous sequence was amplified from a corresponding Ti plasmid and inserted into a kanamycin resistance vector. The homologous sequence was used to integrate the kanamycin resistance gene into the Ti plasmid by homologous recombination.

To construct the pTiBo542C plasmid, the entire virC gene (Genbank accession number AB027257) from the AGL0 Agrobacterium strain was amplified with PCR using the following primers 5' ACAATAATGTGTGTTGT-TAAGTCTTGTTGC 3' (Xd683 SEQ ID NO:3) and 5' CTCAAACCTACACTCAATATTGGTGAG 3' (Xd684

Figure 6:
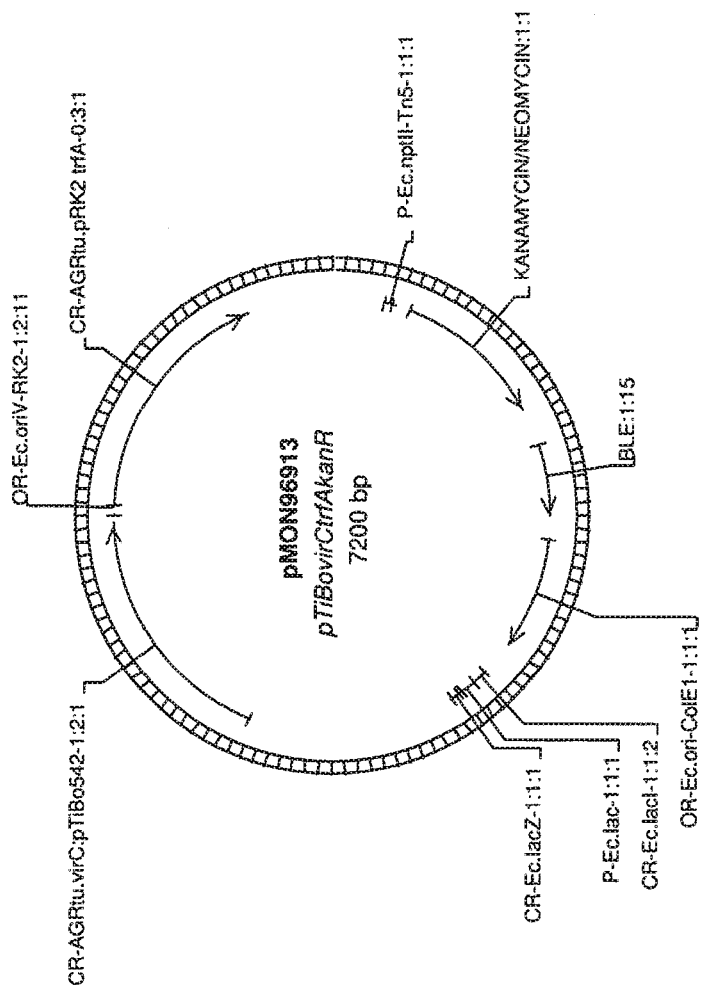
FIG. 6: Schematic map of pMON96913.

SEQ ID NO:4) and Pfu polymerase (STRATAGENE. La Jolla, Calif.) and inserted into the TOPO cloning blunt vector (Invitrogen Carlsbad, Calif.) giving rise to an intermediate vector pMON67402 The intermediate vector was further ligated to a trfA fragment from pCGN11206 digested with PvuII/MscI, which resulted in construct pMON96913 (FIG. 6). The vector was then introduced into the AGL0 Agrobacterium strain by standard electroporation as outlined above, and plated on Kanamycin 50 mg/l LB medium to select for a single crossover event. Since the integration vector is not maintained in AGL0 cells, the resistant colonies were presumably due to integration of the vector into a Ti plasmid by homologous recombination. The resulting strain was designated AGL0C.

Figure 8:
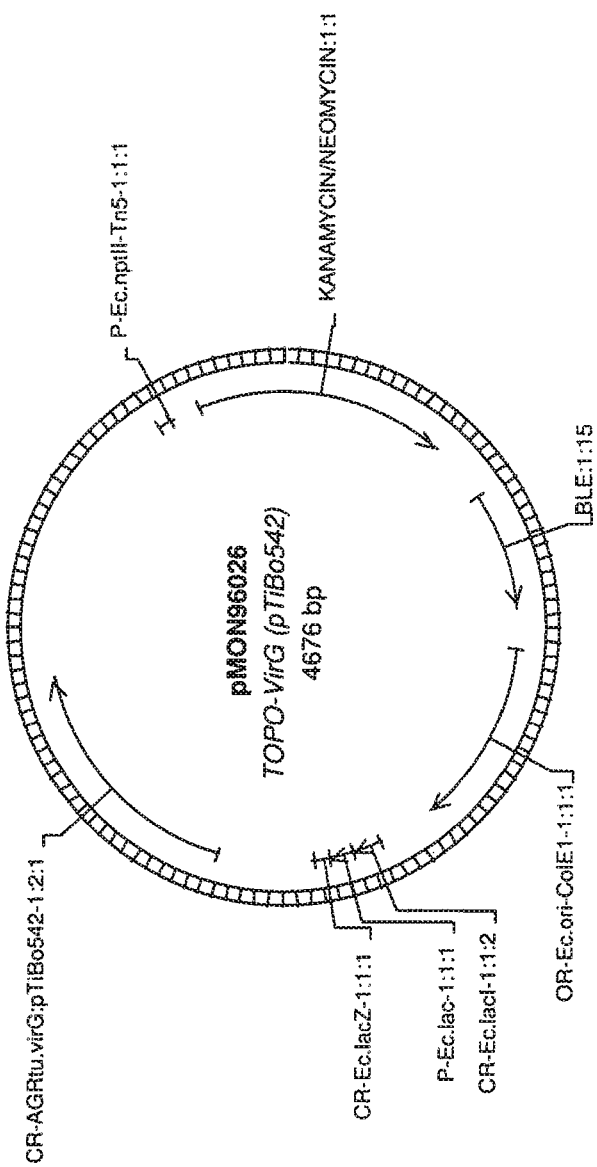
FIG. 8: Schematic map of pMON96026.

Similarly, to construct the pTi542G plasmid, the entire virG sequence (Genbank accession number AB027257) from the AGL0 Agrobacterium strain was PCR amplified using 5' AGATCTGGCTCGCGGCGGACGCAC 3' (Xd681: SEQ ID NO:5) and 5' CGCTCGCGTCATTCTTTGCTGGAG 3' (Xd682; SEQ ID NO:6) with Pfu polymerase and inserted into pMON67402, which resulted in construct pMON96026 (FIG. 8). This vector was introduced into the AGL0 strain by standard electroporation and plated on kanamycin 50 mg/l LB medium to select for a single crossover event. The resulting strain was designated AGL0G.

Figure 7:
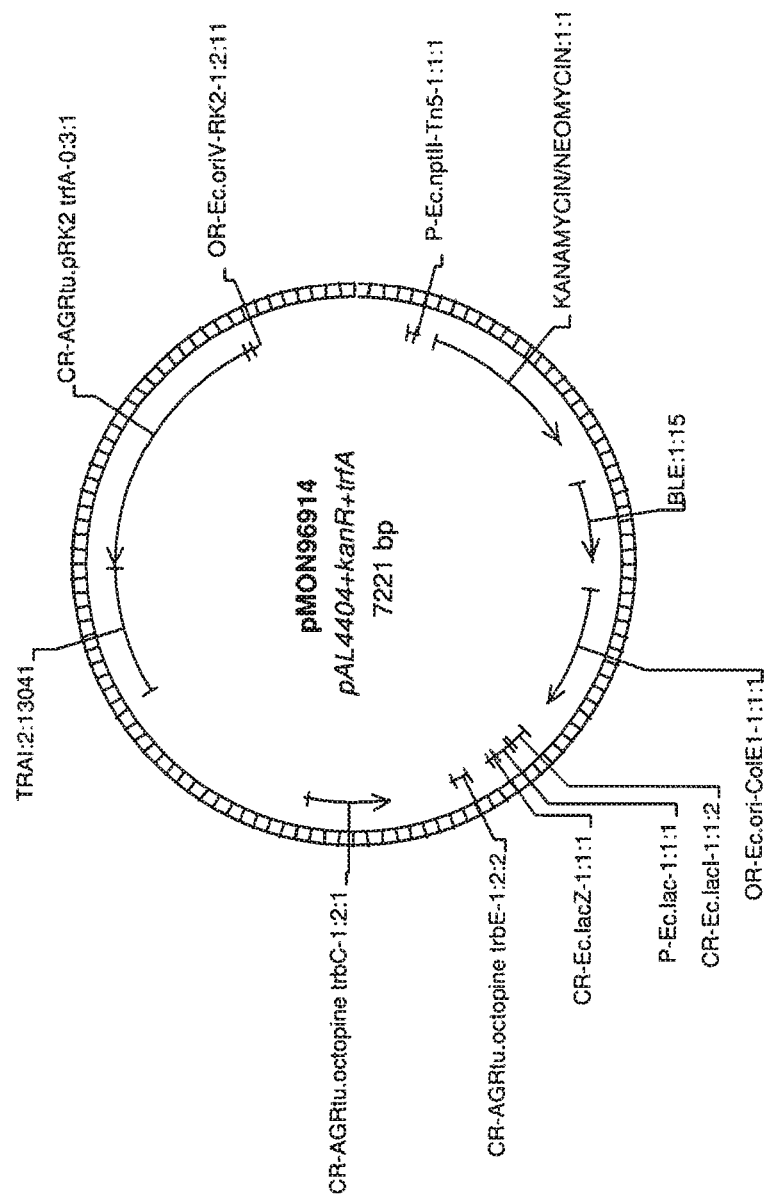
FIG. 7: Schematic map of pMON96914.

In order to construct the pTi4404kan helper plasmid, the traI and trbCE region of octopine Ti plasmid pAL4404 (Genbank accession number NC_002377) from LBA4404 was PCR amplified with primers 5' TCAGCAGGATGACGCCGTTATCG 3' (Xd695; SEQ ID NO:7) and 5' TCTCGCCCGACCAATACCAACAC 3' (Xd696; SEQ ID NO:8) (sequence from Genbank AF242881) with Pfu polymerase, and inserted into pMON67402. The intermediate vector was further ligated to a trfA fragment from pCGN11206 digested with PvuII/MscI, which resulted in construct pMON96914 (FIG. 7). This plasmid vector was introduced into LBA4404 by electroporation and selected on LB medium with kanamycin 50 mg/l to select for a single crossover event.

After a three day culture on solid medium, the kanR resistant colonies were transferred into 2 mls of liquid LB medium with kanamycin 50 mg/l. One microliter of overnight culture was directly amplified with YieldAce® Taq polymerase following manufacturer instructions (Stratagene) with the following primers: 5' GCTGACGGGCCCGGATGAATGTCAGCTACTG 3' (Xd715; SEQ ID NO:9) and 5' GCTCTAGAAATTGTAAGCGTrAATAATTCA-GAAGAACTCGTC 3' (Xd716; SEQ ID NO:10) and integration of the kanamycin resistance gene into Ti plasmids was confirmed. The resulting strain was designated as 4404TIK.

Example 4

Extraction of Ti Plasmids from *Agrobacterium*

The modified Ti plasmids, pTiBo542C, pTiBo542G, pTi4404kan and pTiC58 (ABI), were extracted from the modified *Agrobacterium* strains AGL0C, AGL0G, 4404TIK and ABI, containing the respective plasmids. Five mls of overnight culture in LB with kanamycin 50 mg/l was spun down, resuspended in 400 μl of P1 buffer, mixed with 400 μl of P2 buffer, neutralized with 400 μl P3 buffer (buffers from QIAGEN maxi-prep kit). After 5 min incubation at room temperature, the mixture was spun for 10 min at 12 g at 4° C. Approximately 1200 μl of supernatant was mixed with 800 μl of isopropanol and spun for 10 min at 4° C. The pellet was washed with 70% ethanol once and resuspended in 200 μl of TE without drying. The mega plasmids were subsequently stored at 4° C.

Example 5

Rhizobia Competent Cells and Introduction of Modified Ti Plasmids into Rhizobia

Rhizobia competent cells were prepared according to Garg et al. 1999 with modification. Briefly, one loopful of Rhizobia (e.g. *Rhizobium*) cells from a frozen glycerol stock was grown in 10 mls of TY broth for 24 hours, and then transferred into 500 ml TY broth at 30° C. with vigorous shaking and allowed to grow to mid-logarithmic phase ($OD_{600}$=0.4-0.6). The culture was transferred into two 250 centrifuge tubes, chilled on ice for 15-30 min and centrifuged at 9,000 rpm for 10 min at 4'C to harvest cells. The cell pellet was washed with cold sterile deionized water, and with 10% cold glycerol and resuspended in 10% cold glycerol. The cell suspension was aliquoted at 50 μl/tube for immediate use or frozen in liquid nitrogen and stored at −80'C.

Electroporation of the modified Ti plasmids into Rhizobia strains: Fifty microliters of the competent cells were thawed on ice, mixed with 1 or 2 μls of the prepared Ti plasmid, and kept on ice for 30 min. The mixture was transferred into a chilled 1 mm-gap electroporation cuvette. The electroporation parameters (BIO-RAD Gene Pulser® II) were set as follows: 2 KV/400Ω resistance/25 μF capacity or 1.5 KV/400Ω resistance/25 μF capacity or 1.5 KV/800Ω resistance/10 μF capacity. After electroporation, the cuvette was kept on ice for 5-10 min before adding 1 ml of TY or MAG medium and transferring into a 14-ml Falcon tube. The tube was cultured for 3 hours at 30° C., plated onto TY or MAG solid medium with 50 mg/l kanamycin and cultured at 30° C. for three days to recover resistant colonies.

Confirmation of Rhizobia transformed with Ti plasmids: The kanamycin resistant colonies were transferred into 3 mls of liquid TY or MAG medium with 50 mg/l kanamycin and cultured overnight. One microliter of culture was directly amplified with YieldAce® Taq polymerase following manufacturer's instructions (Stratagene).

To detect pTiBo542C or pTiBo542G in Rhizobia strains, the virC primers 5' ACAATAATGTGTGTTGTTAAGTCT-TGTTGC 3' (Xd683: SEQ ID NO:3) and 5' CAATTG-CATTTTGGCTCTTAATTATCTGG 3' (Xd684a; SEQ ID NO: 1) or virG primers 5' AGATCTGGCTCGCGGCG-GACGCAC 3' (Xd681: SEQ ID NO:5) and 5' CGCTCGCGTCATTCTTTGCTGGAG 3' (Xd682; SEQ ID NO:6) were used to amplify a 2.35 kb or a 1.2 kb fragment, respectively.

For the pTi4404kan plasmid, the following primers were used: 5' GCATGCCCGATCGCGCTCAAGTAATC 3' (Xd699; SEQ ID NO:12) and 5' TCTAGGTC-CCCCCGCGCCCATCG 3' (Xd700; SEQ ID NO:13)) amplifies a 1274 bp virD2 coding sequence for the octopine Ti plasmid; 5' CCATGGATCTTCTGGCAATGAGAAATC 3' (Xd701; SEQ ID NO:14) and 5' GTCAAAAGCTGTT-GACGCTTTGGCTACG 3' (Xd702: SEQ ID NO:15) amplifies a 1602 bp virE2 fragment; 5' ACGGGAGAGGCGGT-GTTTAGTTGC 3' (Xd703; SEQ ID NO:16) and 5' CGATAGCGACAATGCCGAGAACG 3' (Xd704; SEQ ID NO:17) amplifies approximately a 0.9 kb virB1 fragment.

In order to identify the pTiC58 plasmid from the ABI strain, three pairs of primers were used: 5' ATGCCCGATC- GAGCTCAAGTTATC 3' (Xd685; SEQ ID NO:18) and 5' TGAAAGGACACCTCTCCGTTGCTG 3' (Xd686; SEQ ID NO:19) amplifies a 1247 bp virD2 fragment; 5' CCATG-GATCCGAAGGCCGAAGGCAATG 3' (Xd687; SEQ ID NO:20) and 5' CTACAGACTGTTTACGGTTGGGC 3' (Xd688; SEQ ID NO:21) amplifies a 1670 bp virE2 entire coding sequence; 5' GTGAGCAAAGCCGCTGCCATATC 3' (Xd689; SEQ ID NO:22) and 5' TAGAGCGTCTGCT-TGGTTAAACC 3' (Xd690; SEQ ID NO:23) amplifies a 1102 bp partial repA fragment.

Example 6

Media for Bacterial Growth

Media used for Rhizobia growth in the Rhizobia-mediated transformation protocol employed to develop transformed plants were prepared using standard methods known to one skilled in the art. Media formulations are as follows:

| TY medium | |
|---|---|
| | per L |
| Bactotryptone | 5 g/L |
| Yeast extract | 3 g/L |
| CaCl$_2$•2H$_2$O | 0.87 g/L |
| pH 7.0 | |
| For solid TY medium, add 15 g/l Bacto-Agar before autoclaving. | |

MAG Medium Liquid

From USDA *Rhizobium* Collection Center

| | | |
|---|---|---|
| HEPES | 1.3 | g/L |
| MES | 1.1 | g/L |
| Yeast extract | 1 | g/L |
| L-Arabinose | 1 | g/L |
| Potassium gluconate | 1 | g/L |
| KH$_2$PO$_4$ | 0.22 | g/L |
| Na$_2$SO$_4$ | 0.25 | g/L |
| pH 6.6 with KOH | | |

| Autoclave and add the following filter sterilized stock solution: | |
|---|---|
| NH$_4$Cl (16 g/100 ml) | 2 ml/l |
| FeCl$_3$ (0.67 g/100 ml, FS) | 1.0 ml/l |
| CaCl$_2$ (1.5 g/100 ml) | 1.0 ml/l |
| MgSO$_4$ (18 g/100 ml) | 1.0 ml |
| NaMoO$_4$•2H$_2$O (1 g/100 ml) | 1.0 ml/l |
| NiCl$_2$•6H$_2$O (2.2 g/100 ml) | 0.1 ml/l |
| For solid MAG medium, add 15 g/l Bacto-Agar before autoclaving. | |

| LB medium | Per liter |
|---|---|
| Bacto-tryptone | 10 g |
| Bacto-yeast extract | 5 g |
| NaCl | 10 g |
| Adjust pH to 7.5 with sodium hydroxide. | |
| After autoclaving, distribute into culture plate (25 ml/plate) | |
| For solid LB medium, add 15 g/l Bacto-Agar before autoclaving | |

| AB Minimal Medium: | |
|---|---|
| 20x AB Buffer: | |
| K$_2$HPO$_4$ | 60 g/l |
| NaH$_2$PO$_4$ | 20 g/l |
| Autoclave separately | |
| 20x AB Salts (Filter sterilized, keep in dark): | |
| NH$_4$Cl | 20 g/l |
| MgSO$_4$•7H$_2$O | 6 g/l |
| KCl | 3 g/l |
| CaCl$_2$ | 0.2 g/l |
| FeSO$_4$•7H$_2$O | 50 mg/l |
| pH to 7 before autoclaving | |
| Combine 50 ml AB Buffer and 50 ml AB Salts with 900 ml sucrose-water (final concentration of sucrose in one liter is 0.5%). | |

| 1x AB-TY Induction medium: | |
|---|---|
| Glucose | 5 g |
| 20x AB buffer | 50 ml |
| 20X AB Salt stock | 50 ml |
| TY medium | 20 ml |
| Add sterile water to | 1000 ml |
| Adjust to pH 5.4 with | 100 mM MES |
| Add 100 µM acetosyringone (1M stock in DMSO; add 1 µl stock/10 ml medium after suspending bacteria) | |

| ATA Medium for vir Induction in *Rhizobium*: | |
|---|---|
| The ATA (AB minimal medium + TY + Arabinose) medium was modified from AB-TY medium using arabinose and potassium gluconate to replace glucose. The growth rate of all Rhizobia is almost doubled in this medium. The bacteria produced much less polysaccharide in this medium and the bacterial pellets were much tighter. | |
| L-Arabinose | 1 g/L |
| Potassium gluconate | 1 g/L |
| 20x AB buffer | 50 ml |
| 20x AB salt stock | 50 ml |
| TY medium | 20 ml |
| Add sterile water to | 1000 ml |
| pH 5.4 with 100 mM MES | |
| Add 200 µM acetosyringone (1M stock in DMSO) after resuspending bacteria. | |

Example 7

Crop Transformation Vectors for Use with Modified Rhizobia Strains

Figure 2:
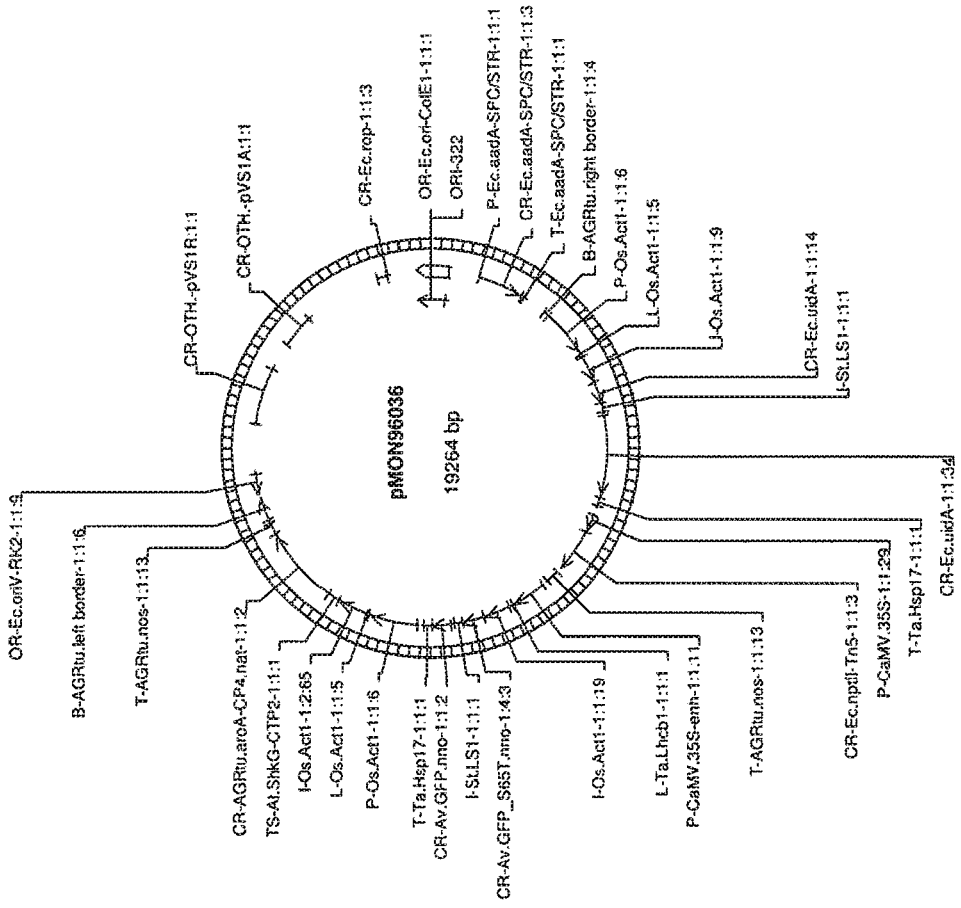
FIG. 2: Schematic map of pMON96036.
Figure 3:
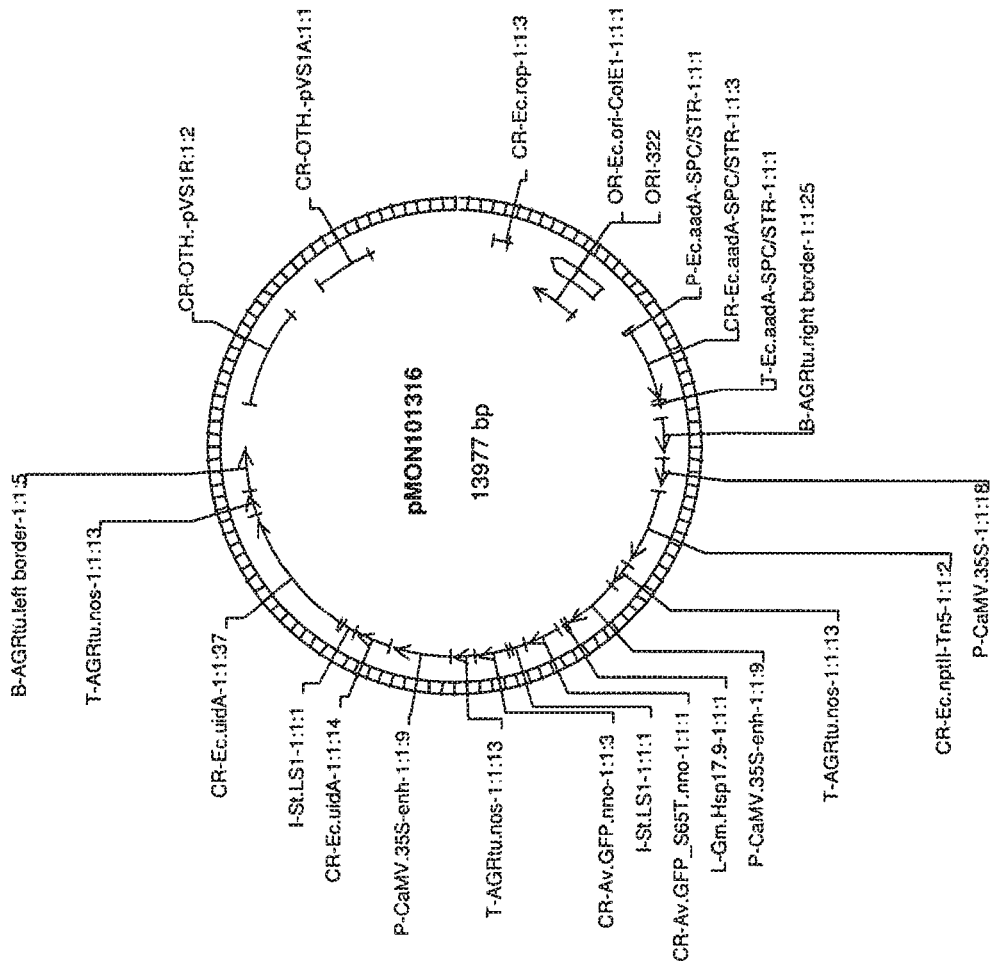
FIG. 3: Schematic map of pMON101316.

*Rhizobium* transformation vectors were constructed using standard molecular techniques known to those skilled in the art. Plasmid constructs pMON96033 (FIG. 1; for soybean and canola transformation), pMON96036 (FIG. 2; for corn transformation), or pMON101316 (FIG. 3; for cotton transformation) were employed. All three constructs contain a pVS1 replication origin, and either GUS, GFP, or both reporter genes. Recombinant plasmids were transferred into various modified Rhizobia strains by electroporation and confirmed by restriction enzyme digestion of miniprep DNA.

The FMV CP4 gene used in constructing the plasmids has a promoter from Figwort Mosaic Virus (FMV) followed by the CP4syn gene, a synthetic gene encoding CP4 EPSP synthase. See, U.S. Pat. No. 5,633,435, which is incorporated by reference herein. EPSP synthase, when expressed, confers a substantial degree of glyphosate resistance upon the plant cell and plants generated there from. The e35s GUS gene is a β-glucuronidase gene, which is typically used as a histochemical marker, behind the e35S promoter. The FMV GUS gene is the FMV promoter with GUS. The NOS NPTII gene has a neomycin phosphotransferase gene, which confers resistance to kanamycin, behind the promoter for the nopaline synthase gene (NOS). The Act 1 GFP gene has an actin promoter from rice and the gene for green fluorescence protein, which is a screenable marker. The e35s GFP gene is the gene for green fluorescence protein behind the e35S promoter. Overnight cultures of a Rhizobia strain containing the plasmid used were grown to log phase and then diluted to a final optical density of 0.3 to 0.6.

Example 8

Rhizobia-Mediated Soybean Transformation

Transformation was performed using an organogenesis process, as described by Martinell et al. (U.S. Pat. No. 7,002,058), with modifications, pMON96033 containing the GUS and CP4 genes were transferred into various modified Rhizobia strains (e.g. *Rhizobium* sp., *Mesorhizobium* sp., *Sinorhizobium* sp.) by electroporation. Single colonies were recovered on MAG or TY medium with 50 mg/l spectinomycin and 50 mg/l kanamycin and inoculated in 20-50 mls of liquid TY medium with the same selection in a shaker at 30° C. at 200 rpm. The presence of plasmid in the Rhizobia culture was verified by restriction enzyme digestion of mini-prepared plasmid from 10 ml culture. The remaining liquid culture was mixed with glycerol to a final concentration of 20%, aliquoted and stored at −80° C. as seed cultures.

To prepare Rhizobia inoculum, 0.25-1 ml frozen seed culture was inoculated into 250 or 500 mls of TY medium with the same antibiotic selection as above and grown overnight at 28° C. with shaking at 200 rpm to mid-log growth phase. The culture was spun down and directly suspended in an inoculation medium (INO medium) at the concentration of $OD_{660}$ about 0.3.

Induced Rhizobia culture was also used in soybean transformation. To induce the Rhizobia, the overnight culture was resuspended in AB-TY medium at an $OD_{660}$ of about 0.3 and acetosyringone was added to a final concentration of 100 µM. The culture was further shaken overnight at 28° C., spun down and re-suspended in the inoculation medium (INO medium) to a concentration of $OD_{660}$ about 0.3.

Soybean cultivar A3525 (U.S. Pat. No. 7,002,058) was used for Rhizobia-mediated transformation. The method was modified for Rhizobia-mediated transformation as follows. Soybean seeds were germinated at room temperature in BGM medium and meristem explants from soy mature seeds were excised by machine (U.S. Application 20050005321). Soybean meristem explants in a PLANT-CON lid were mixed with Rhizobia suspension in INO medium and sonicated in a W-113 Sonicator (Honda Electronics Co., Ltd, Aichi, Japan). After sonication, the explants were co-cultured in the same PLANTCON for 1-11 days at 23° C. with a 16/8 hour light-dark photo period. The explants were then transferred onto the surface of the WPM selection medium containing 75 LM glyphosate. After 2 weeks, explants were transferred again to 75 µM glyphosate solid WPM medium. Shoots with fully expanded trifolia were recovered after 6-10 weeks post-inoculation and rooted in BRM medium (optionally with fungicide) containing 0.1 mg/l IAA and 25 µM glyphosate selection. The rooted plantlets were transferred to the greenhouse for maturity.

TABLE 2

Media components for soy transformation.

| amount/L | Compound |
|---|---|
| BGM medium for soybean seed germination | |
| 0.505 g | Potassium nitrate |
| 0.24 g | Ammonium nitrate |
| 0.493 g | Magnesium sulfate |
| 0.176 g | Calcium chloride |
| 27.2 mg | Potassium phosphate monobasic |
| 1.86 mg | Boric acid |
| 5.07 mg | Manganese sulfate |
| 2.58 mg | Zinc sulphate |
| 0.249 mg | Potassium iodide |
| 0.216 mg | Sodium Molybdate |
| 0.0008 mg | Copper sulphate |
| 0.0008 mg | Cobalt chloride stock |
| 3.36 mg | Disodium EDTA |
| 2.49 mg | Ferrous sulphate |
| 1.34 mg | Thiamine HCl |
| 0.5 mg | Nicotinic acid |
| 0.82 mg | Pyridoxine HCl |
| 20 g/L | Sucrose (Ultra Pure) |
| 125 mg | Cefotaxime |
| pH | 5.6 |
| INO medium for soy co-culture | |
| 1/10x of Gamborg B5 medium micronutrient and vitamin components; 2/5x of macronutrients | |
| 1 g | Potassium Nitrate ($KNO_3$) |
| 30 g | Glucose |
| 3.9 g | MES (pH 5.4) |
| After autoclaving, lipoic acid added to inoculum to a final concentration of 250 µM | |
| SOY WPM shooting medium | |
| 2.41 g | WPM Powder (PhytoTech Laboratories) |
| 20 g | Sucrose (Ultra Pure) |
| 1.29 g | Calcium Gluconate (Sigma) |
| 4.0 g | AgarGel (pH 5.6) |
| mL/L | Post-autoclaving ingredients |
| 4 mL | Cefotaxime (50 mg/mL) |
| 1 ml | Ticarcillin (100 mg/ml) |
| 5 mL | Carbenicillin (40 mg/mL) |
| 0.15 mL | Glyphosate (0.5 FS Stock) (0.075 mM) |
| BRM rooting medium | |
| amount/L | Compound |
| 2.15 g | MS Powder (Phytotech) |
| 0.1 g | myo-Inositol |
| 2 mg | Glycine |
| 0.5 mg | Nicotinic acid |
| 0.5 mg | Pyridoxine HCl |
| 0.1 mg | Thiamine HCl |
| 30 g | Sucrose (Ultra Pure) |
| 10 ml | L-Cysteine (10 mg/ml) |
| 8 g | Washed Agar |
| mL/L | Post-autoclaving ingredients |
| 5.0 | IAA (0.033 mg/ml in 1 mM KOH) |
| 1 mL | Ticarcillin (100 mg/ml) |
| 0.05 mL | Glyphosate (0.5 FS Stock) (0.025 mM) |

The binary vector pMON96033 was transferred into Rhizobia strains and co-cultivated with soybean meristem explants, and GUS positive results were observed (Table 3 and FIG. 4). *S. meliloti, S. fredii. M. loti* and one *R. leguminosarum* showed T-DNA delivery into soybean explants demonstrated by small blue spots of GUS activity. Transgenic soybean plants were obtained from Rhizobia-mediated transformation experiments with various strains (Table 4). The transgenic nature of these soybean plants were confirmed by transgene copy number assay, where most of the transformants revealed 1-2 copy simple integration pattern. (Table 5).

TABLE 3

Transient Expression of gus Gene with Rhizobia-mediated T-DNA Delivery in soybean meristem explants.*

| Strain | Origin | Transient GUS assay |
|---|---|---|
| RL4404 | *Rhizobium leguminosarum* strain Madison + pAL4404 | + |
| 2370LBA | *Rhizobium leguminosarum* strain USDA2370 + pTiBo542C | + |
| 2370G | *Rhizobium leguminosarum* strain USDA2370 + pTiBo542G | + |
| SF4404 | *Sinorhizobium fredii* USDA205 + pAL4404 | + |
| SF542C | *Sinorhizobium fredii* USDA205 + pTiBo542C | + |
| SM542C | *Mesorhizobium loti* USDA3471 + pAL4404 | + |
| ML4404 | *Mesorhizobium loti* USDA3471 + pAL4404 | + |
| ML542G | *Mesorhizobium loti* USDA3471 + pTiBo542G | + |

*Transient assays were performed after 4 day co-culture period.

TABLE 4

Rhizobia-mediated soy transformation summary.

| Strains | Soy Explants | Rooted Plants | TF |
|---|---|---|---|
| RL 4404 | 3705 | 2 | 0.05% |
| SF 4404 | 5553 | 2 | 0.04% |
| SM 542C | 2555 | 1 | 0.04% |

TABLE 5

Copy Number Assay of Transgenic Plants from Rhizobia-mediated Transformation*

| NOS copy | RL4404 | SF4404 | SM542C |
|---|---|---|---|
| 0 copy | 0 | 0 | 1 |
| 1-2 copy | 1 | 2 | 0 |
| >2 copy | 0 | 0 | 0 |
| Total Plant | 1 | 2 | 1 |

*Copy number was analyzed by INVADER method (Third Wave Technologies, Madison, WI) using a nos probe and compared with an internal genome control.

Figure 5:
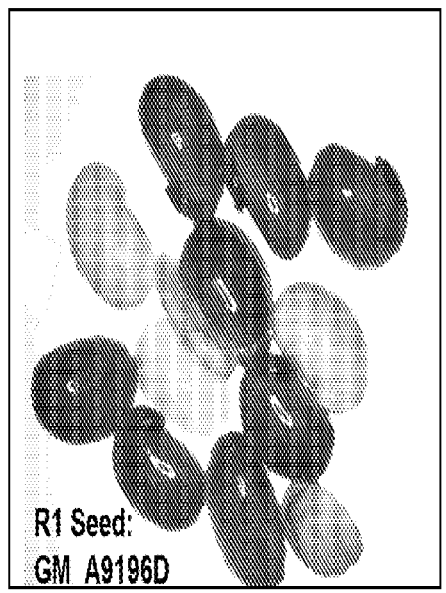
FIG. 5: Germline transmission of gus transgene in soy produced through *Rhizobium*-mediated transformation.

To test if the gus transgene was transmitted to the seed progeny, seeds of two soy transgenic lines derived from Rhizobia-mediated transformation were stained in GUS solution (FIG. 5). The GM_A9196D line was found to have one copy of the linked nos gene as assayed by the INVADER method. Twelve R1 seeds from this line were assayed for GUS by histochemical staining after imbibition and removal of seed coat, and 9 were GUS positive, indicating a segregation ratio of 3:1 for one copy insert.

Example 9

Rhizobia-Mediated Canola Transformation

A. *Rhizobium* Inoculum Preparation:

Rhizobia strains with pMON96033 were used for canola transformation. The Rhizobia strains with the vector from a glycerol stock were inoculated into 10 mls of TY medium with 50 mg/l kanamycin and 50 mg/l spectinomycin in a 50 ml Falcon tube and shaken at 28° C. overnight at 200 rpm. The overnight Rhizobia culture was pelleted by centrifugation and resuspended in MG/L liquid medium. (MG/L broth: Mannitol 5 g/l, L-glutamic acid 1 g/l, $KH_2PO_4$ 250 mg/l, NaCl 100 mg/l, $MgSO_4.7H_2O$ 100 mg/l, biotin 1 µg/l, yeast extract 2.5 g/l, pH7.0). The $OD_{600}$ was between 0.05-0.1.

B. Canola Explant Preparation and Co-Cultivation:

Canola transformation was done according to U.S. Pat. No. 5,750,871 and Radke et al., 1992. About 0.25 g of canola seed, cv. Ebony, was transferred into a 1.5-ml Eppendorf tube and wetted with 95% ethanol. To sterilize the seeds, 1 ml of 1% sodium hypochlorite solution was added for 30 min. The bleaching solution was replaced with distilled water and the seeds were rinsed several times. The seeds were spread onto ⅒ MS germination medium and kept in a Percival incubator at 24° C. with a 16 hour light photo period.

Seed Germination Medium (⅒ MS Medium):

⅒×MS minimal organics medium (Gibco BRL; final sucrose 0.3%), pyridoxine 50 µg/l, nicotinic acid 50 µg/l, glycine 200 µg/l, PHYTAGAR (Gibco Invitrogen) 6 g/l, pH 5.8; 20). Etiolated seedlings from 7-14 days old cultures were used as the explant source.

Figure 9:
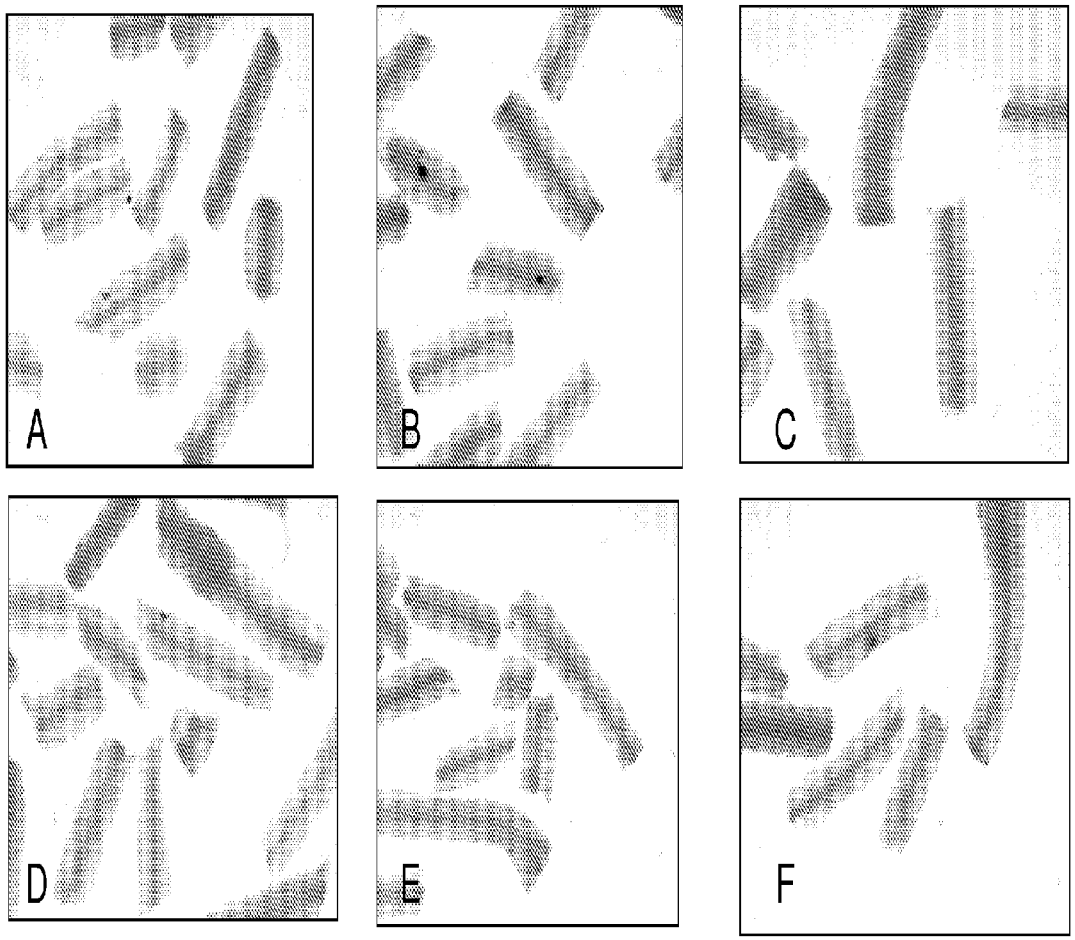
FIG. 9: Rhizobia-mediated transformation of canola with several strains as shown by GUS transient assay. A) ML542C (22.4%); B) RL2370G (33.3%); C) RL2370LBA (20%); D) SF542C (30.5%); E) SF4404 (20.6%); and F) SM542C (13%). The % of explants with GUS positive sectors are shown in parentheses.

Explants were inoculated in $1\times10^8$ bacteria/ml. *Rhizobium* suspension was drawn off, and the inoculated explants were placed onto co-cultivation plates on top of filter paper, and incubated for about 2 days at 24° C. in continuous light. Co-cultivated explants were assayed for gus expression and found to contain blue spots indicating transformation of canola cells (FIG. 9).

Co-Cultivation Medium (MS-1):

MS salts (Caisson Laboratories, Logan, Utah), myo-inositol 100 mg/l, thiamine-HCl 1.3 mg/l, $KH_2PO_4$ 200 mg/l, 2,4-D 1 mg/l, sucrose 3%, PHYTAGAR (Gibco Invitrogen) 7 g/l, pH 5.8.

Figure 10:
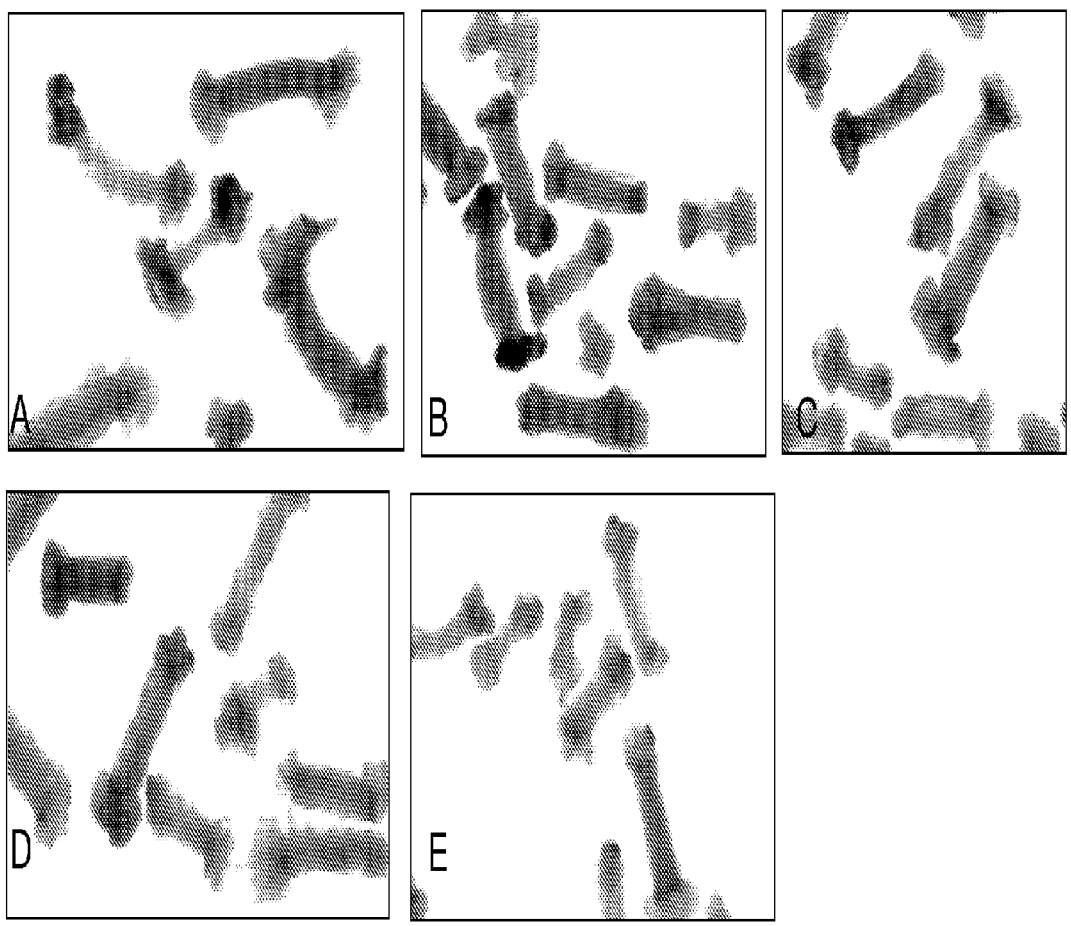
FIG. 10: Stable transgenic canola calli transformation with several strains of Rhizobia. A) ML542C (50%); B) RL2370G (21%): C) RL2370LBA (67%); D) SF542C (36%); and E) SM542C (73%). The % of explants with GUS positive sectors are shown in parentheses.

C. Callus Induction:

Co-cultivated explants were transferred to Callus Induction (B5-1) medium, for 6 days at 24° C. in continuous light at ~100 µE/m²/s. Five strains from *M. loti, R. leguminosarum, S. fredii* and *S. meliloti* showed efficient gene transfer into canola explants with frequency of gus positive explants ranging from 21% to 73% (FIG. 10).

Callus Induction Medium (B5-1):

Gamborg's B5 salts (Caisson Labs). B5 vitamins (1 mg/l nicotinic acid, 1 mg/l pyridoxine-HCl, 10 mg/l thiamine-HCl), 100 mg/l inositol, 1 mg/l 2,4-D, sucrose 3%, carbenicillin (PhytoTechnology, Shawnee Mission, Kans.) adjusted to final potency of 325 mg/l, 50 mg/l Timentin, 7 g/l PHYTAGAR (Gibco Invitrogen), pH5.8.

Figure 11:
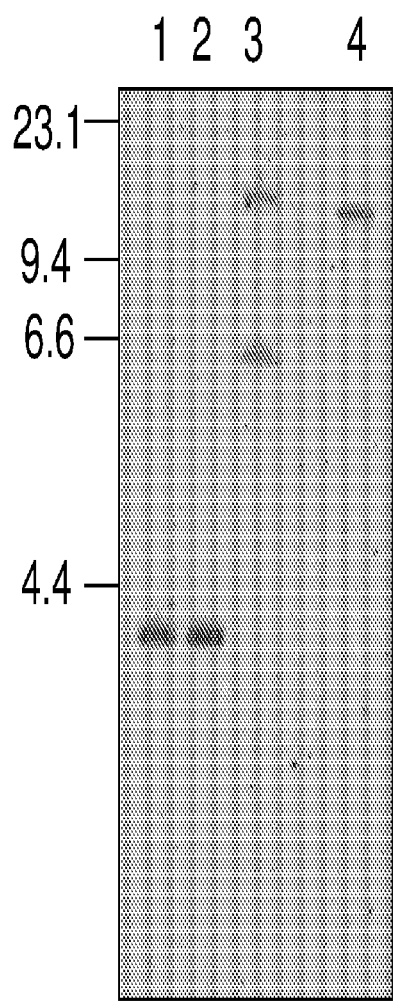
FIG. 11: Southern blot detection of the CP4 transgene in canola plants derived from *Rhizobium*-mediated transformation. Lane 1: BN_A22 line; lane 2: BN_A24 line; lane 3: BN_A28 line; and lane 4: BN_A35 line.

D. Shoot Regeneration and Selection:

Explants having callus were transferred to Shoot Regeneration medium (B5BZ) with $AgNO_3$ and incubated at 24° C. in continuous light of 100 µE/m²/s for 14 days. Explants were next transferred to Shoot Regeneration medium (B5BZ) without $AgNO_3$. Shoots regenerated from glyphosate-selected calli were harvested ~every two weeks. An example of early shoots showing gus expression is shown in FIG. 11.

Shoot Regeneration Medium with Silver Nitrate (B5BZ+3Ag):

Gamborg's B5 salts (Caisson Labs), B5 vitamins (1 mg/l nicotinic acid, 1 mg/l pyridoxine-HCl, 10 mg/l thiamine-HCl), 100 mg/l inositol, BAP 3 mg/l (Sigma), zeatin 1 mg/l (Sigma), $AgNO_3$, 3 mg/l (Sigma), 45 mg/l glyphosate (Monsanto, 96.5% dry acid,), sucrose 1%, carbenicillin (Phyto-Technology) with potency adjusted to 325 mg/l, 50 mg/i Timentin, PHYTAGAR (Gibco Invitrogen) 7 mg/i, pH 5.8.

Shoot Regeneration Medium (B5BZ):

Gamborg's B5 salts (Caisson Labs), B5 vitamins (1 mg/l nicotinic acid, 1 mg/l pyridoxine-HCl, 10 mg/l thiamine- HCl), 100 mg/l inositol, BAP 3 mg/l (Sigma, zeatin 1 mg/l (Sigma), 45 mg/i glyphosate, sucrose 1%, carbenicillin (PhytoTechnology) with potency adjusted to 325 mg/l, Timentin 50 mg/l, PHYTAGAR (Gibco Invitrogen) 7 mg/l, pH 5.8.

E. Shoot Harvest:

Green shoots at least 0.5 cm in length were trimmed to isolate the main axis. Trimmed shoots were placed on Shoot Harvest medium (B5-0). Shoots were transferred to Rooting medium after 2 weeks.

Shoot Harvest Medium (B5-0):

Gamborg's B5 salts (Caisson Labs), B5 vitamins (1 mg/i nicotinic acid, 1 mg/l pyridoxine-HCl, 10 mg/l thiamine-HCl), 100 mg/l inositol, carbenicillin (PhytoTechnology) with potency adjusted to 195 mg/l, sucrose 1%, PHYTAGAR (Gibco Invitrogen) 6 g/l, pH 5.8.

F. Shoot Growth and Rooting:

Green shoots were transferred to Rooting medium (B5-0+2IBA). Shoots remained on Rooting medium until they formed roots Shoots were maintained at 24° C., 16 hours light/day, ~100 uE/m²/s.

Rooting Medium (B5-0+2IBA):

Gamborg's B5 salts (Caisson Labs), B5 vitamins (1 mg/l nicotinic acid, 1 mg/l pyridoxine-HCl, 10 mg/l thiamine-HCl), 100 mg/l inositol, IBA 2 mg/l (indole-3-butyric acid, Sigma) 150 mg/l cefotaxime (PhytoTechnology), sucrose 1%, PHYTAGAR (Gibco Invitrogen) 6 g/l, pH 5.8.

G. Transgene Detection and Transformation Frequency:

Total genomic DNA was extracted from greenhouse grown canola plants, digested with a single cutter BglII, and hybridized with DIG-labeled CP4 probe. Four lines were confirmed to be transgenic (FIG. 11). The transformation frequency is summarized in the Table 6.

TABLE 6

Canola transformation frequency (TF) with *Rhizobium* strains

| Strains | Explants | GUS/CP4 positive | TF |
|---------|----------|------------------|------|
| RL 2370G | 150 | 2 | 1.33 |
| SF 542 | 120 | 1 | 0.83 |
| SM542C | 120 | 1 | 0.83 |

Example 10

Rhizobia-Mediated Cotton Transformation Through Embryogenesis

A. Rhizobia Inoculum Preparation:

pMON101316 was electroporated into Rhizobia strains, verified by restriction digestion of mini-prepared DNA and stored at −80° C. The Rhizobia strains with the vector from the glycerol stock were inoculated into 10 mls of TY medium with kanamycin (50 mg/l) and spectinomycin (50 mg/l) in a 50 ml Falcon tube and shaken at 28° C. overnight at 200 rpm. The overnight Rhizobia culture was pelleted by centrifugation, resuspended in 20 mls of MS0 liquid medium and centrifuged again. The pellet was resuspended in 20 mls of MS0 medium. The washed Rhizobia was diluted in MS0 to an $OD_{600}$ of about 1.0 for inoculation.

B. Explant Preparation:

Cotton transformation was done essentially according to U.S. Publ. 2004087030. Seven days after seedlings were germinated, etiolated cotton seedlings from cultivar Coker were removed from a dark Percival incubator. The hypocotyls from the PHYTATRAYs were harvested and placed in a sterile Petri dish containing sterile MSO to prevent the tissue from drying out. Hypocotyls were cut into small explants.

C. Inoculation and co-cultivation:

Using a sterile forceps, explants were transferred to sterile Petri dishes, and Rhizobia inoculum was added. Explants were left in a sterile hood for 20 minutes, with swirling to ensure good contact of all explants with the Rhizobia inoculum. The Rhizobia inoculum solution was then aspirated out and explants were gently blotted with sterile filter paper The inoculated hypocotyl pieces were placed onto culture plates. Co-culture of the plates of explants, covered with a plastic bag, was performed in a Percival incubator set at about 22-24° C., with a 10 hour light/14 hour dark photoperiod for 2 days.

Figure 12:
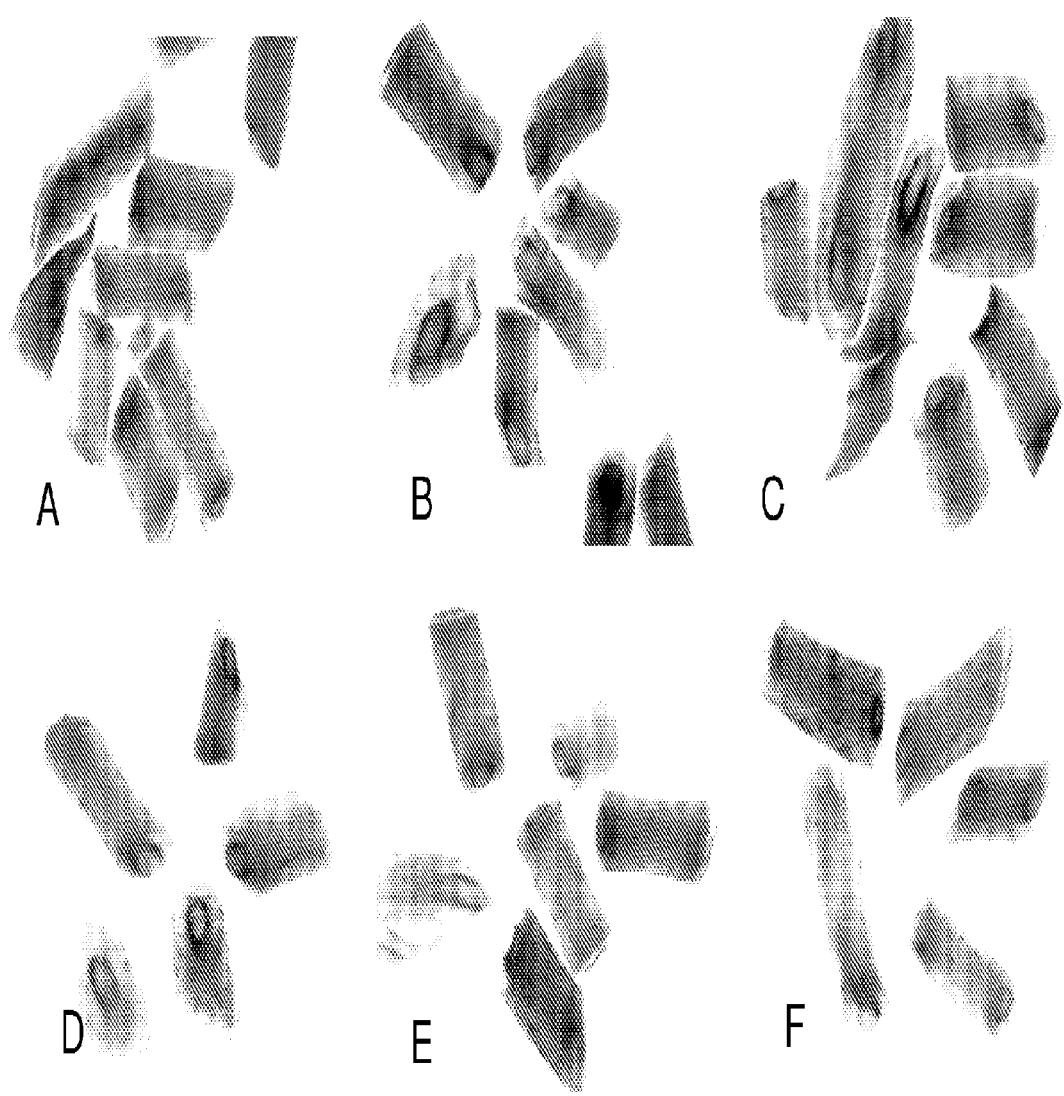
FIG. 12. Cotton transformation by Rhizobia containing pMON101316: A) ML542C (47.8%); B) RL2370G (56%); C) RL2370LBA (31.4%); D) SF542C(23.2%); E) SF4404 (31.5%); and F) SM542C (44.4%). RL2370 was used as a negative control; *Agrobacterium tumefaciens* ABI strain was used as a positive control. The percentage of GUS staining positive explants are written in parentheses above.

D. Stable Transformation Through Embryogenesis:

Two days post inoculation, cotton explant pieces were stained with X-gluc to test for GUS transient expression (FIG. 12). Blue spots in hypocotyls indicate the expression of the gus gene and transformation of cotton cells. In order to obtain stable transformed plants, hypocotyl explants were transferred onto a plate containing UMSEL1629 selection medium, containing the appropriate selection agent. The plates were then covered with PARAFILM and cultured 28° C. with a 16/8 hr. (day/night) photo period.

Figure 13:
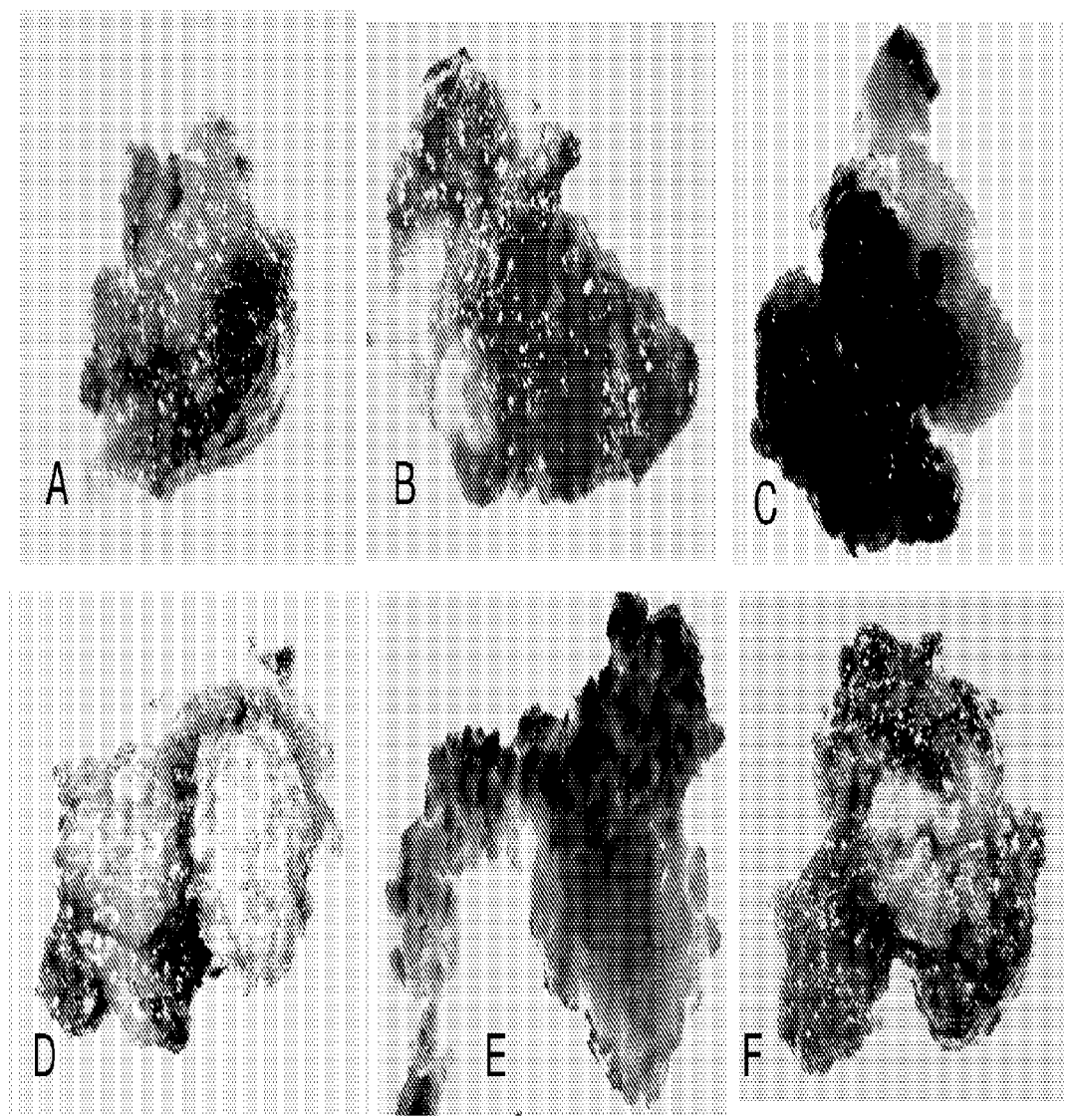
FIG. 13: Stable transformation of cotton calli by several Rhizobia strains: A) ML542C; B) SF542C; C) SM542C; D) SF4404; E) RL2370LBA; and F) RL2370G.

The stably transformed calli were confirmed by X-Gluc staining for gus expression after 4 weeks on the selection medium (FIG. 13). Four weeks after the initial transfer to selection medium, all the hypocotyls were transferred to UMSEL 1788 medium, PARAFILMed and cultured for 7 days. Then the explants were transferred back onto UMSEL1629 for 4 weeks at 28° C. with a 16/8 hr. (day/night) photo period.

Approximately 4 weeks after the second transfer on UMSEL1629, depending upon the growth rate of the callus, clumps of calli were recovered and were transferred to UMO plates. Individual plates are then labeled, covered with PARAFILM, and cultured at 28° C. in continuous dark.

Six to eight weeks after the callus has been on UMO the calli are subcultured onto fresh UMO medium and cultured at 28° C. in continuous dark. After 6-10 weeks on UMO, embryogenic callus (EC) is ready to be harvested from independent callus lines on UMO and is transferred to TRP+ medium. Every 3-5 weeks, for approximately 3 months, actively growing tissue and small embryos on TRP+ plates are transferred to fresh TRP+ medium and cultured at 28° C. in continuous dark. Embryos are transferred to SHSU medium in Petri plates and covered with PARAFILM. Plates are cultured at 28° C. in a Percival with a 16/8 (day/night) photo period with maximum lighting (shelf and side lights). The embryos may be subcultured on same medium one more time until germination. Plantlets recovered are cultured in a Percival or warm room at 28° C. with a 16/8 (day/night) photo period.

Figure 14:
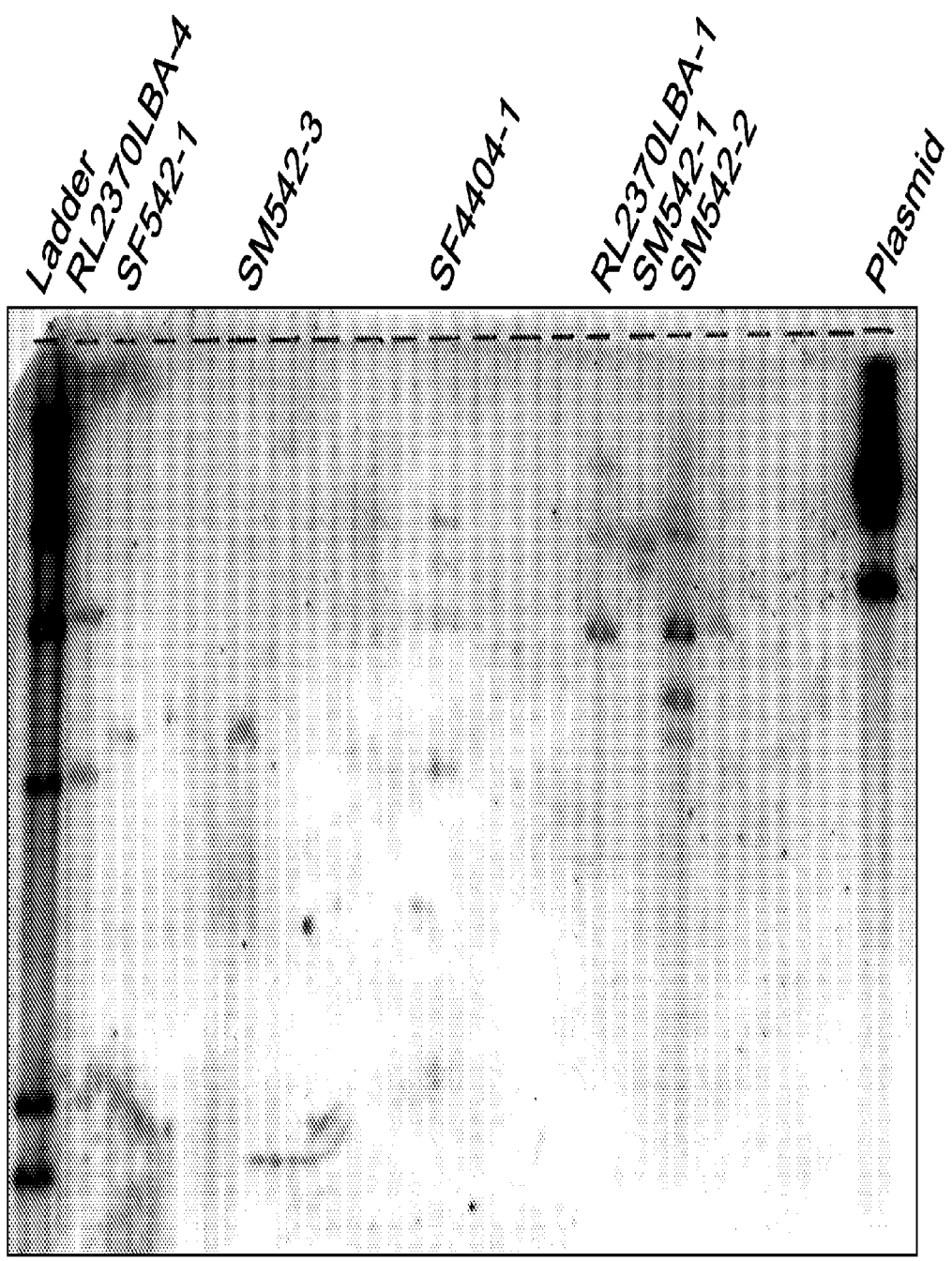
FIG. 14: Detection of the gus transgene by Southern hybridization in cotton calli derived from *Rhizobium*-mediated transformation. RL2370LBA: *R. leguminosarum* 2370 with LBA4404 Ti helper plasmid; SF542: *Sinorhizobium fredii* 205 with pTiBo542 helper plasmid from AGL0 strain; and SF4404: *Sinorhizobium fredii* 205 with LBA4404 Ti helper plasmid.

E. Molecular Analysis of Transgenic Nature of Cotton Calli Derived from *Rhizobium*-Mediated Transformation:

Genomic DNA was extracted from callus tissue, digested with a single cutter BamHI, fractionated in 1% agarose gel, and transferred onto Hybond™ membrane (e.g. Appligen-Oncor, Illkirch, France; or Amersham-Pharmacia Biotech). A DIG labeled gus probe was used to detect the presence of the transgene as an indicator of transformation. Six lines of cotton calli, derived from *S. meliloti*, *S. fredii* and *R. leguminosarum* transformation with Ti helper plasmid, were found to contain the gus gene (FIG. 14).

F. Media for Cotton Culture:

Recipe for 1 L of UMSEL—

4.33 g MS salts, 2 ml 500× B5 vitamins, 0.1 ml 2.4-D (1 mg/ml), 1 ml kinetin (0.5 mg/ml), 30 g glucose, pH 5.8, 2.5 g PHYTAGEL, 1.7 ml carbenicillin (250 mg/ml), 1 ml cefotaxime (100 mg/ml), plus selection agent: kanamycin 40 mg/L final concentration. Carbenicillin, cefotaxime and selective agents were added post-autoclaving.

Recipe for 1 L of UMSEL1788:—

4.33 g MS salts, 2 ml 500× B5 vitamins, 0.1 ml 2,4-D (1 mg/ml), 1 ml kinetin (0.5 mg/ml), 30 g glucose, pH 5.8, 2.5 g PHYTAGEL, 1.7 ml (250 mg/ml) carbenicillin, 1 ml (100 mg/ml) cefotaxime, plus selection agent: kanamycin 40 mg/L final concentration and 0.1 g sucrose dissolved in 100 ml water. Carbenicillin, cefotaxime and selective agents were added post-autoclaving.

Recipe for 1 L of UMSEL1629:—

4.33 g MS salts, 2 ml 500× B5 vitamins, 0.1 ml 2,4-D (1 mg/ml), 1 ml kinetin (0.5 mg/ml), 30 g glucose, pH 5.8, 2.5 g PHYTAGEL, 1.7 ml (250 mg/ml) carbenicillin, 1 ml (100 mg/ml) cefotaxime, plus selection agent: kanamycin 40 mg/L final concentration. Carbenicillin, cefotaxime and selective agents were added post-autoclaving.

Recipe for 1 L of UMO—

4.33 g MS salts, 2 ml 500× B5 vitamins, 30 g glucose, pH 5.8, 3.5 g GELRITE, 1.7 ml (250 mg/ml) carbenicillin, 1 ml (100 mg/ml) cefotaxime, 100 mg/l ascorbic acid, plus selection agent: kanamycin 50 mg/L final concentration.

Recipe for 1 L of TRP+—

4.33 g/l MS salts, 2 ml 500× B5 vitamins, 1.9 g/l $KNO_3$, 30 g/l glucose, 0.1 g/l casein hydrolysate, 3.5 g GELRITE, pH 5.8.

Recipe for 1 L of SHSU—

100 ml Stewart & Hsu Majors (10×), 10 ml Stewart & Hsu Minors (100×), 1.5 ml iron (100×), 10 ml Stewart & Hsu Organics (100×), 5 g glucose, 50 mg/l benlate, 2.2 g GELRITE, pH 6.8 (Stewart & Hsu, 1977).

Example 11

Rhizobia-Mediated Corn Transformation

A. *Rhizobium* Inoculum Preparation and Media Composition:

pMON96036 containing CP4, GUS and gfp expression cassettes was used for corn transformation. The vector was electroporated into various modified Rhizobia strains, verified, and stored at −80° C. Rhizobia containing the vector in a glycerol stock were streaked out on solid TY medium supplemented with antibiotics (kanamycin 40 mg/L and spectinomycin 31 mg/L), and incubated at 28° C. for 2 days.

Two days before Rhizobia inoculation of the maize immature embryos, one loopful of cells from a Rhizobia culture plate was inoculated into 25 mL of liquid TY medium supplemented with 62 mg/L of spectinomycin and 40 mg/L of kanamycin in a 250 mL flask. The flask was placed on a shaker at approximately 150-200 rpm and 27-28° C. overnight. The Rhizobia culture was then diluted (1 to 5) in the same liquid medium and put back on the shaker. Several hours later, one day before inoculation, the Rhizobia cells were spun down at 3500 rpm for 15 min. The bacterial cell pellet was re-suspended in AB-TY or ATA induction broth with 200 μM of acetosyringone and 50 mg/L spectinomycin and 25 mg/L kanamycin and the cell density was adjusted to 0.2 at $OD_{600}$. The bacterial cell culture (50 mL in each 250 mL flask) was then put back on the shaker and grown overnight. On the morning of inoculation day, the bacterial cells were spun down and washed with liquid ½ MS VI medium (U.S. Publ. 20040244075) supplemented with 200 μM of acetosyringone. The bacterial culture was centrifuged and the cell pellet was re-suspended in ½ MS PL medium (U.S. Publ. 20040244075) with 200 μM of acetosyringone and the cell density was adjusted to 1.0 at $OD_{660}$ for inoculation. Reagents are commercially available and can be purchased from a number of suppliers (see, for example Sigma Chemical Co., St. Louis, Mo.).

B. Corn Embryo Isolation and *Rhizobium* Co-Cultivation:

For Rhizobia-mediated transformation, ears containing immature corn (*Zea mays*) embryos were isolated and transformed by bacterial co-culture as generally described by Cai et al. (U.S. Patent Application Publication 20040244075), except that the immature embryos were isolated from surface sterilized ears and directly dropped into the prepared Rhizobia cell suspension. After the Rhizobia cell suspension was removed, the immature embryos were transferred onto the co-culture medium (U.S. Publ. 20040244075).

Figure 15:
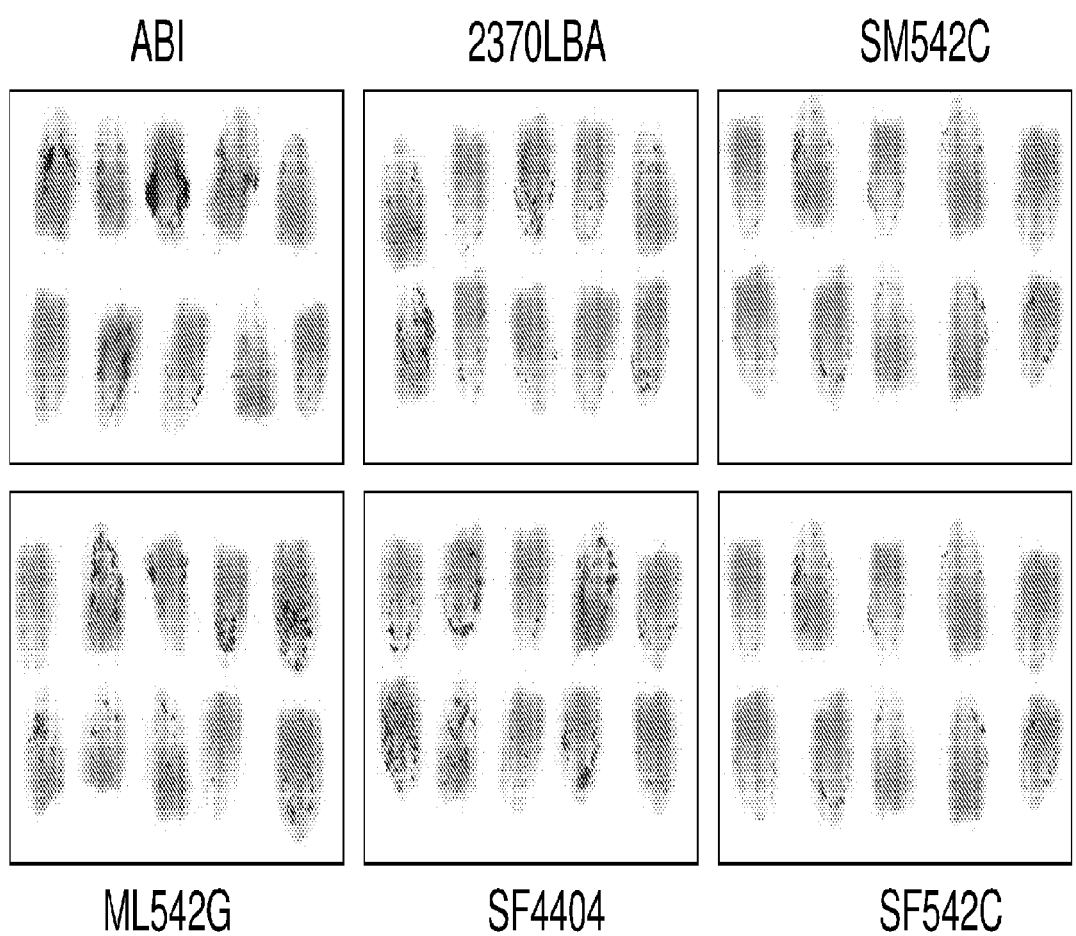
FIG. 15: Rhizobia-mediated corn transformation as shown by transient expression of a gus gene in corn immature embryos. ABI: *A. tumefaciens*; RL2370LBA: *Rhizobium leguminosarum* USDA2370 with LBA4404 Ti plasmid; SM542C: *Sinorhizobium meliloti* USDA1002 with pTiBo542; ML542G: *Mesorhizobium loti* with pTiBo542; SF4404: *Sinorhizobium fredii* USDA205 with LBA4404 Ti plasmid; SF542C: *Sinorhizobium fredii* USDA205 with pTiBo542. All strains contained pMON96036 and were induced in ATA medium pH5.4.

To investigate GFP transient expression, the co-cultivated corn embryos were directly placed under a microscope with fluorescence light for GFP observation. Alternatively, 10 randomly picked embryos after co-cultivation were transferred into 1.5 ml Eppendorf tube and stained with X-gluc solution overnight at 37° C. for gus transient expression. FIG. 15 represents GUS transient expression of corn immature embryos transformed with five *Rhizobium* strains of *R. leguminosarum. M. loti, S. fredii* and *S. meliloti* compared to *Agrobacterium tumefaciens* strain ABI using ATA induction medium.

It was noted that routine AB minimal medium used for *Agrobacterium* growth and induction does not efficiently support Rhizobia growth. Rhizobia *inoculums* did not show significant growth in AB minimal medium without any selection after one week shaking with 220 rpm at 28° C. Inclusion of 20 ml TY medium in AB minimal medium dramatically improves Rhizobia growth rate; while replacing glucose in AB-TY medium with L-arabinose and potassium gluconate in ATA medium decreases polysaccharide production, resulting into tighter pellets. The change of carbon source in induction medium significant improves gus transient expression with Rhizobia strains in corn.

Figure 16:
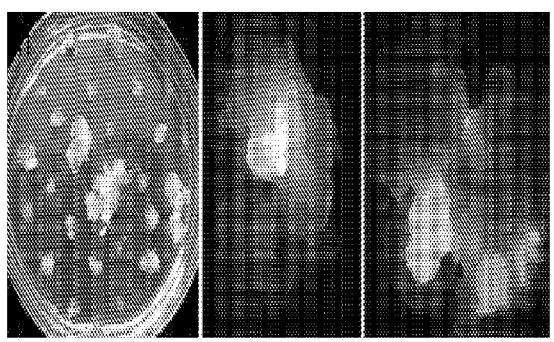
FIG. 16: Corn calli expressing the gfp marker after transformation with Rhizobia strains.
Figure 16:
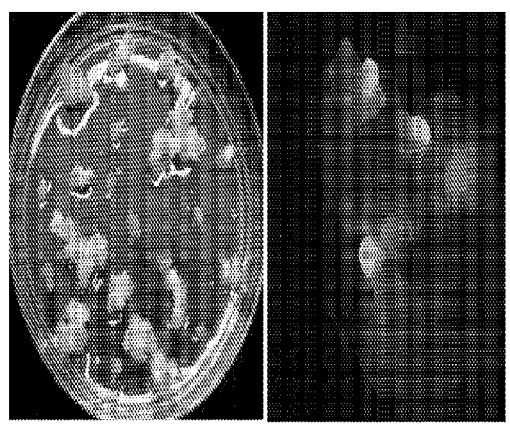
Figure 16:
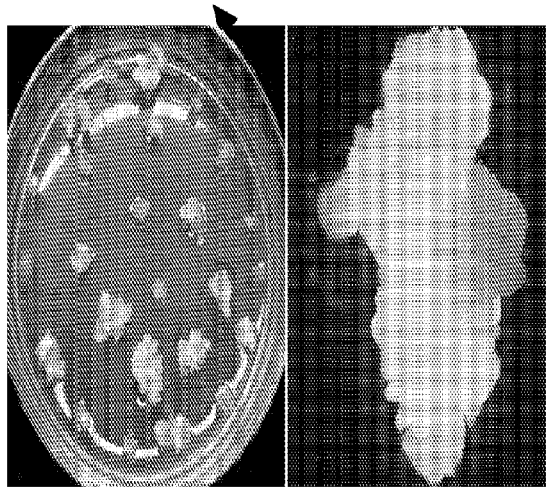
Figure 16:
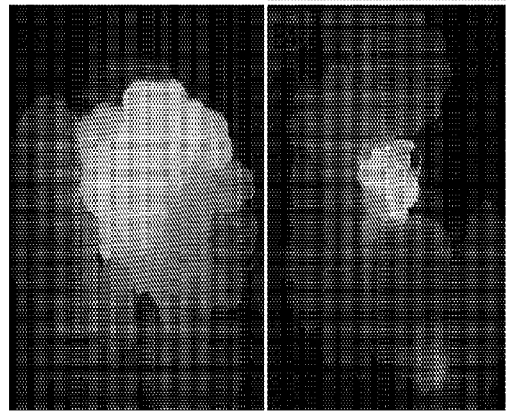

C. Callus Induction and Regeneration of Transgenic Plants:

After co-cultivation, transformation was continued essentially as described in U.S. Publ. 20040244075, with modifications of selection conditions as appropriate. The embryos were transferred onto a modified MS medium (U.S. Publ. 20040244075) supplemented with 250 mg/L carbenicillin and 0.1 mM glyphosate Stably transformed calli with gfp expression were observed from the *M. loti, S. fredii* and *S. meliloti* stains used in transient assay at this stage (FIG. 16). Representative transformation frequencies are shown in Table 7.

TABLE 7

Corn transformation frequency with different Rhizobia strains.

| Induction medium | Rhizobia Strain | Embryos | Transgenic plants | TF |
|---|---|---|---|---|
| AB induction | ML4404 | 177 | 3 | 1.69% |
| | ML542G | 154 | 2 | 1.30% |
| | ABI | 83 | 7 | 8.40% |
| ATA Induction | ML542G | 112 | 2 | 1.78% |
| | SF4404 | 116 | 6 | 5.17% |
| | SF542C | 124 | 2 | 1.61% |
| | SM542C | 134 | 1 | 0.75% |
| | 2370LBA | 139 | 0 | 0% |
| | ABI | 100 | 1 | 1% |

Figure 17:
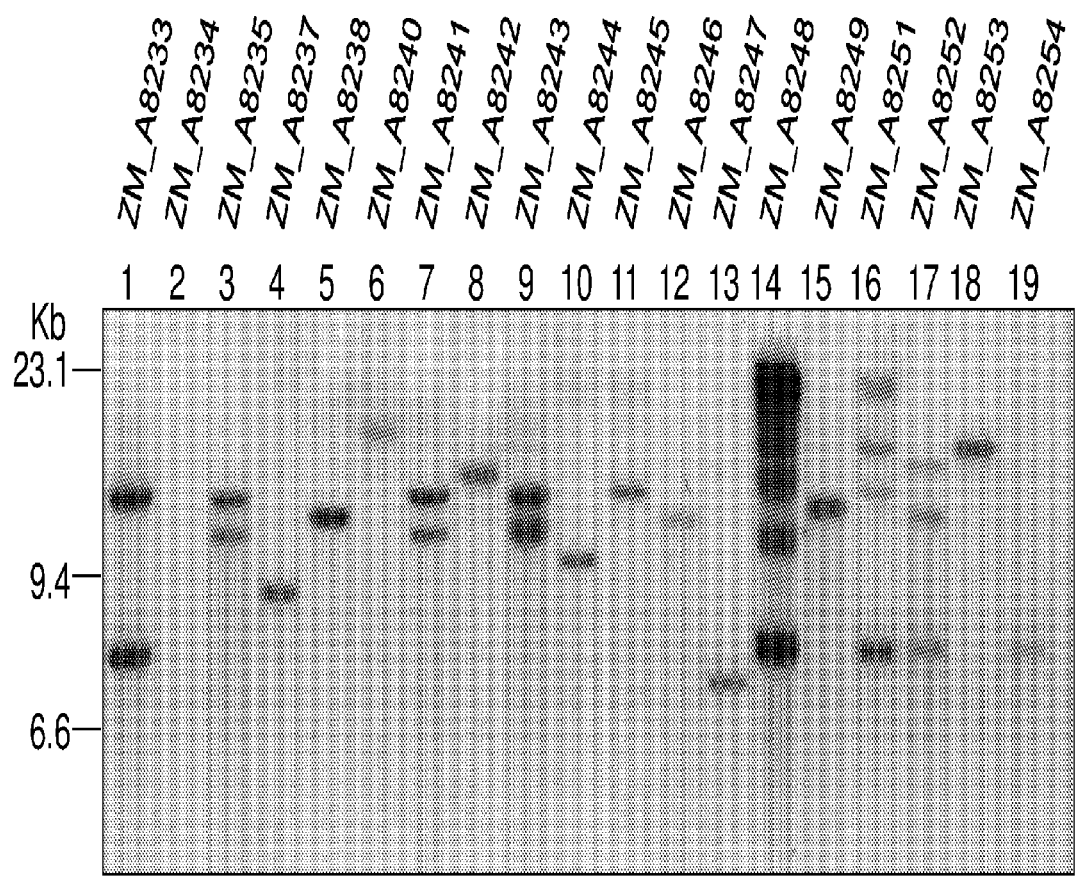
FIG. 17: Southern hybridization analysis of transgene integration in corn plants derived from *Rhizobium*-mediated transformation. DIG-labeled gus probe was used to detect the transgene. Lane 1-2 and 11-12: lines derived after transformation with *M. loti* ML542G/pMON96036; lane 3-9: lines derived after transformation with *A. tumefaciens* ABI control; lane 13-17: lines derived after transformation with *S. fredii* SF4404/pMON96033; Lane 18-19: lines derived after transformation with *S. fredii* SF542C/pMON96036.

D. Molecular Analysis of Transgenic Plants Derived from Rhizobia-Mediated Transformation:

Total genomic DNA was isolated from greenhouse grown corn plants and digested with a single cutter BamHI to estimate transgene copy number. A DIG-labeled gus probe was used to hybridize with the genomic DNA. The transgenic nature of putatively transformed tissues was confirmed for all lines but one (FIG. 17).

E. Germline Transmission of Transgenes in the Transgenic Corn Plants:

The flowering transgenic corn plants were either selfed or outcrossed with the parental line of the corn genotype used for transformation (line LH244). Dry seeds were imbibed in water for 1 day for gus staining or 2 days for gfp counting, gus or gfp expression and segregation in the transgenic R1 seeds were confirmed (Table 8).

TABLE 8

Transgene expression in the transgenic corn R1 seeds.

| Transgenic line | seed # | GFP + seeds/ seeds assayed | Gus + seeds/ Seeds assayed | Rhizobia strain |
|---|---|---|---|---|
| ZM_A8232 | 112 | 9/20 | 6/7 | ML542G |
| ZM_A8232/LH244 | 112 | 4/20 | | ML542G |
| ZM_A8234 | 48 | 0/10 | 0/20 | ML542G |
| ZM_A8246 | 133 | 12/20 | 5/5 | ML542G |
| ZM_A8247 | 148 | 4/20 | 1/3 | SF4404 |
| LH244/ZM_A8247 | 150 | | 13/20 | SF4404 |
| ZM_A8248 | 75 | 0/20 | 4/6 | SF4404 |
| LH244/ZM_A8249 | 104 | | 13/20 | SF4404 |
| LH244/ZM_A8249 | 275 | | 9/20 | SF4404 |
| LH244/ZM_A8251 | 148 | | 7/20 | SF4404 |
| LH244/ZM_A8251 | 123 | | 5/20 | SF4404 |
| LH244/ZM_A8251 | 108 | | 4/20 | SF4404 |
| ZM_A8252 | 137 | 9/20 | 4/6 | SF4404 |
| ZM_A8255 | 78 | 10/20 | | SM542C |
| LH244/ZM_A8245 | 31 | | 2/10 | ML542G |
| LH244/ZM_A8253 | 138 | | 10/20 | SF542C |
| LH244/ZM_A8253 | 67 | | 5/20 | SF542C |
| LH244/ZM_A8254 | 72 | | 8/20 | SF542C |
| LH244/ZM_A8254 | 100 | | 6/20 | SF542C |
| LH244/ZM_A8235 | 81 | | 12/20 | ABI |
| LH244/ZM_A8235 | 116 | | 13/20 | ABI |
| LH244/ZM_A8235 | 161 | | 8/20 | ABI |
| ZM_A8237/LH244 | 294 | 7/20 | 5/7 | ABI |
| ZM_A8244/LH244 | 250 | 4/20 | | ABI |
| ZM_A8240 | 14 | | 3/4 | ABI |
| ZM_A8240/LH244 | 86 | 7/20 | | ABI |
| ZM_A8238 | 31 | | 10/10 | ABI |
| LH244/ZM_A8238 | 90 | | 10/20 | ABI |
| ZM_A8256 | 53 | 3/10 | | ABI |
| LH244/ZM_A8256 | 55 | | 8/20 | ABI |

Example 12

Rhizobia-Mediated Crop Transformation Through Conjugal Transfer System

An oriT-dependent plasmid conjugal transfer system in *Rhizobium* and related species may also be used to deliver a gene of interest (GOI) into plant cells and subsequently be integrated into the plant genome. A homogenous or heterogeneous conjugal transfer system could be used for the gene transfer. Transgenic plants could then be regenerated with selectable markers through an established tissue culture system. Rhizobia strains may include *Sinorhizobium* spp., *Mesorhizobium loti, Rhizobium leguminosarum* and *Rhizobium* sp. NGR234, among others.

REFERENCES

The following references, to the extent that they provide exemplary procedural or other details supplementary to those set forth herein, are specifically incorporated herein by reference.

U.S. Pat. No. 4,761,373; U.S. Pat. No. 4,810,648; U.S. Pat. No. 5,013,659; U.S. Pat. No. 5,094,945; U.S. Pat. No. 5,106,739: U.S. Pat. No. 5,107,065; U.S. Pat. No. 5,141,870; U.S. Pat. No. 5,229,114; U.S. Pat. No. 5,273,894: U.S. Pat. No. 5,276,268; U.S. Pat. No. 5,322,938; U.S. Pat. No. 5,352,605; U.S. Pat. No. 5,359,142; U.S. Pat. No. 5,362,865; U.S. Pat. No. 5,378,619; U.S. Pat. No. 5,378,824; U.S. Pat. No. 5,424,412; U.S. Pat. No. 5,463,175; U.S. Pat. No. 5,512,466; U.S. Pat. No. 5,530,196; U.S. Pat. No. 5,543,576; U.S. Pat. No. 5,561,236; U.S. Pat. No. 5,563,055; U.S. Pat. No. 5,591,616; U.S. Pat. No. 5,605,011; U.S. Pat. No. 5,608,149; U.S. Pat. No. 5,627,061; U.S. Pat. No. 5,633,435; U.S. Pat. No. 5,633,437; U.S. Pat. No. 5,637,489; U.S. Pat. No. 5,641,876; U.S. Pat. No. 5,646,024; U.S. Pat. No. 5,659,122; U.S. Pat. No. 5,689,041; U.S. Pat. No. 5,750,871; U.S. Pat. No. 5,750,876; U.S. Pat. No. 5,767,366; U.S. Pat. No. 5,837,848; U.S. Pat. No. 5,850,019; U.S. Pat. No. 5,859,347: U.S. Pat. No. 5,869,720; U.S. Pat. No. 5,958,745; U.S. Pat. No. 5,981,834; U.S. Pat. No. 5,985,605; U.S. Pat. No. 5,998,700; U.S. Pat. No. 6,011,199; U.S. Pat. No. 6,040,497; U.S. Pat. No. 6,051,753; U.S. Pat. No. 6,072,103: U.S. Pat. No. 6,080,560; U.S. Pat. No. 6,140,075; U.S. Pat. No. 6,140,078; U.S. Pat. No. 6,166,292; U.S. Pat. No. 6,171,640: U.S. Pat. No. 6,175,060; U.S. Pat. No. 6,177,611; U.S. Pat. No. 6,225,105; U.S. Pat. No. 6,228,623; U.S. Pat. No. 6,232,526; U.S. Pat. No. 6,252,138; U.S. Pat. No. 6,271,443; U.S. Pat. No. 6,294,714; U.S. Pat. No. 6,380,462; U.S. Pat. No. 6,380,466; U.S. Pat. No. 6,384,301; U.S. Pat. No. 6,414,222; U.S. Pat. No. 6,426,446; U.S. Pat. No. 6,426,447; U.S. Pat. No. 6,429,357; U.S. Pat. No. 6,429,362; U.S. Pat. No. 6,433,252; U.S. Pat. No. 6,437,217: U.S. Pat. No. 6,444,876; U.S. Pat. No. 6,459,018; U.S. Pat. No. 6,476,295; U.S. Pat. No. 6,483,008; U.S. Pat. No. 6,489,461; U.S. Pat. No. 6,495,739; U.S. Pat. No. 6,506,559; U.S. Pat. No. 6,531,648; U.S. Pat. No. 6,537,750; U.S. Pat. No. 6,538,178; U.S. Pat. No. 6,538,179; U.S. Pat. No. 6,538,181; U.S. Pat. No. 6,541,259; U.S. Pat. No. 6,576,818; U.S. Pat. No. 6,589,767; U.S. Pat. No. 6,596,538; U.S. Pat. No. 6,635,806; U.S. Pat. No. 6,613,963; U.S. Pat. No. 6,653,530; U.S. Pat. No. 6,660,849; U.S. Pat. No. 6,706,950: U.S. Pat. No. 6,723,837; U.S. Pat. No. 6,770,465; U.S. Pat. No. 6,774,283; U.S. Pat. No. 6,812,379; U.S. Pat. No. 6,822,141; U.S. Pat. No. 6,828,475; U.S. Pat. No. 7,002,058; U.S. Pat. No. 7,132,528; U.S. Pat. No. 7,151,204; U.S. Pat. No. RE37,543

U.S. Patent Publ. 20020168707; U.S. Patent Publ. 20030028917: U.S. Patent Publ. 20030083480; U.S. Patent Publ. 20030115626; U.S. Patent Publ. 20030135879; U.S. Patent Publ. 20040177399; US Patent Publ. 20040244075; U.S. Patent Publ. 20050005321; U.S. Patent Publ. 20050022261; U.S. Patent Publ. 20050289667; U.S. Patent Publ. 20050289672; U.S. Patent Publ. 20060200878; U.S. Patent Publ. 20060162010; U.S. Patent Publ. 20060236420;

Beringer, *J. Gen. Microbiol.*, 84:188-198, 1974.
Bevan et al., *Nature*, 304:184-187, 1983.
Bird et al., *Biotech Gen. Eng. Rev.*, 9:207-227, 1991.
Bravo-Angel et al., *J. Bacteriol.*, 181:5758-5765, 1999.
Broothaerts et al., *Nature*, 433:629-633, 2005.
Buchanan-Wollaston, *Nature*, 328:172-175, 1987.
Callis et al., *Plant Physiol.*, 88:965-968, 1988.
Carrington and Freed, *J. Virol.*, 64(4): 1590-1597, 1990.
Chandler et al., *Plant Cell.* 1:1175-1183, 1989.
Chen et al., *J. Bacteriol.* 184:4838-4845, 2002.
Chu et al., *Scientia Sinica* 18:659, 1975.
Corruzzi et al., *EMBO J.* 3:1671-1679, 1984.

Dekeyser et al., *Plant Physiol.*, 90:217-223, 1989.
Della-Cioppa et al., *Bio/Technology*, 5:579-584, 1987.
Depicker et al., *J. Mol. Appl. Genet.* 1:561-573, 1982.
Dube and Thomson. *Plasmid.*, 50:1-11, 2003.
Dube et al., *Plant Mol. Biol.*, 55(4):531-539, 2004.
Duncan et al., *Planta*, 165:322-332, 1985.
Ebert et al., *Proc. Nat. Acad. Sci. USA* 84:5745-5749, 1987.
European Appln. 0385 962;
European Appln. 275 957
Farrand et al., *Int. J. Svst. Evol. Microbiol.*, 53:1681-1687, 2003.
Fraley et al., *Bio/Technology*, 3:629-635, 1985.
Fraley et al., *Proc. Natl. Acad. Sci. USA.*, 80:4803-4807, 1983.
Freiberg et al., *Nature*, 387:394-401, 1997.
Gamborg et al., *Erp. Cell Res.*, 50:151, 1968.
Garg et al., *Appl. Env. Microbiol.*, 65:2802-2804, 1999.
Gibson and Shillitoe, *Mol. Biotech.* 7:125-137, 1997.
Hiei et al., *Plant J.;* 6:271-282, 1994.
Hiei et al., *Plant. Mol. Biol.*, 35(1-2):205-218, 1997.
Hoekema et al., *Nature*, 303:179, 1983.
Hooykaas et al. *J. Gen. Microbiol.* 98:477-484, 1977.
Ishida et al., *Nature Biotechnol.*, 14:745-750, 1996.
Komari et al., *Curr. Opin. Plant Biol.*, 1:161-165, 1998.
Kuhlemeier et al., *Plant Cell*, 1:471-478, 1989.
Lawton et al., *Plant Mol. Biol.* 9:315-324, 1987.
Lazo et al., *Bio/Technol.*, 9:963-967, 1991.
Linsmaier and Skoog, *Physiol. Plant.*, 18:100, 1965.
Long, *Plant Physiol.*, 125:69-72, 2001.
Marcotte et al., *Plant Cell*, 1:969-976, 1989.
McCormac et al., *Euphytica*, 99(1):17-25, 1998.
McCown and Lloyd, *Hort. Science*, 16:453, 1981.
Miki and McHugh, *J. Biotechnol.* 107 193-232, 2004.
Murashige and Skoog, *Physiol. Plant*, 15:473-497, 1962.
Nitsch and Nitsch, *Science*, 163:85-87, 1969.
Noel et al., *Can. J. Microbiol.* 42:279-283, 1996.
Odell et al., *Nature* 313:810-812, 1985.
Okita et al., *J Biol Chem.* 264:12573, 1989.
PCT Appln. WO 87/04181; PCT Appln. PCT Appln. WO 89/00193; PCT Appln. WO 99/027116; PCT Appln. WO 04/009761; PCT Appln. WO 04/074443; PCT Appln. WO 05/003362
Perez-Mendoza et al., *J. Bacteriol.*, 186(17):5753-5761, 2004.
Radke et al., *Plant Cell Rep.* 11:499-505, 1992.
Rogers et al., *Methods Enzymol.* 153:253-277, 1987.
Sambrook et. al., Molecular Cloning. A Laboratory Manual, Cold Spring Harbor Press, 1989
Schaffner et al., *Plant Cell*, 3:997-1012, 1991.
Schenk and Hildebrandt, *Can. J. Bot.*, 50:199-204, 1972.
Schrammeijer et al., *Plant Cell Reports*, 9: 55-60, 1990.
Shadenkov et al., *Mol. Biol.*, 30:272-275, 1996.
Southern, *Mol. Biol.*, 98:503-517, 1975
Spaink, H. P. et al., (ed.), The *Rhizobiaceae*. Kluwer Academic Publishers, Dordrecht, The Netherlands, 1998.
Stewart & Hsu. *Planta.* 137:113-117, 1977.
Tingay et al., *Plant J.*, 11(6): 1369-1376, 1997.
Tun-Garrido et al., *J. Bacteriol.*, 185(5):1681-1692, 2003.
Turner et al., *FEMS Microbiol. Ecol.*, 42(2):227-234, 2002.
Uchimiya and Murashige, *Plant Physiol.*, 15:473, 1962.
Walker et al., *Proc. Natl. Acad. Sci. USA*, 84:6624, 1987.
Weller et al, *Pl. Pathol.* 54:799-805, 2005.
Weller et al., *Appl. Env. Microbiol.*, 70:2779-2785, 2004.
Wuni et al., *Plant Cell*, 1:961-968, 1989.
Yang et al. *Proc. Natl. Acad. Sci. USA*, 87:4144-4148, 1990.
Zhang and Meyer, *Mol. Microbiol.*, 25:509-516, 1997.
Zhou et al., *Plant Cell Rep.*, 15:159-163, 1995.

What is claimed is:

1. A method for transforming a canola plant cell, comprising:
    (a) contacting at least a first canola plant cell with a cell of a *Rhizobia* bacterium other than *Agrobacterium* sp. comprising: (i) a first nucleic acid comprising a vir gene region of a Ti plasmid wherein the vir gene region acts to introduce a nucleic acid of interest into the plant cell in a VirD2-dependent manner; and (ii) a second nucleic acid comprising one or more T-DNA border sequence(s) operably linked to a nucleic acid of interest; and
    (b) selecting at least a first canola plant cell transformed with the nucleic acid of interest.

2. The method of claim 1, wherein the first nucleic acid lacks left and/or right T-DNA border sequences.

3. The method of claim 1, wherein the *Rhizobia* cell is grown in the presence of acetosyringone or other compound that induces vir gene function prior to contacting the canola plant cell.

4. The method of claim 1, wherein the *Rhizobia* cell is selected from the group consisting of: *Rhizobium* spp., *Sinorhizobium* spp., *Mesorhizobium* spp., *Phyllobacterium* spp. *Ochrobactrum* spp. and *Bradyrhizobium* spp.

5. The method of claim 4, wherein the *Rhizobia* cell is *Rhizobium leguminosarum*.

6. The method of claim 5, wherein the *Rhizobia* cell is *R. leguminosarum* bv. *trifolii*, *R. leguminosarum* bv. *phaseoli* or *Rhizobium leguminosarum*. bv. *viciae*.

7. The method of claim 1, wherein the canola plant cell is comprised in an explant from a plant seed, seedling, callus, cell suspension, cotyledon, meristem, leaf, root, or stem; and the explant is contacted with the bacterium.

8. The method of claim 7, wherein the explant comprises an embryonic meristem; callus; cell suspension; cotyledon; or tissue from leaves, roots, or stems.

9. The method of claim 1, wherein the first and second nucleic acids are introduced into the bacterium by electroporation.

10. The method of claim 1, wherein selecting a canola plant cell transformed with the nucleic acid of interest is carried out in the absence of a selection agent.

11. The method of claim 1, wherein selecting a canola plant cell transformed with the nucleic acid of interest comprises culturing the plant cell in the presence of a selection agent, wherein the nucleic acid of interest confers tolerance to the selection agent or is operably linked to a further nucleic acid that confers tolerance to the selection agent.

12. The method of claim 11, wherein the selection agent is glyphosate, kanamycin, bialaphos or dicamba.

13. The method of claim 12, wherein the nucleic acid of interest or further nucleic acid encodes EPSP synthase.

14. The method of claim 13, wherein the EPSP synthase protein is CP4.

15. The method of claim 11, wherein the selection agent is glyphosate.

16. The method of claim 1, wherein the nucleic acid of interest is not physically linked to a selectable marker gene.

17. The method of claim 16, wherein the marker gene and the nucleic acid of interest genetically segregate in progeny of a canola plant regenerated from the canola plant cell transformed with the nucleic acid of interest.

18. The method of claim 1, wherein the bacterium comprises at least a third nucleic acid comprising a further nucleic acid of interest and wherein the canola plant cell is transformed with the third nucleic acid.

19. The method of claim 1, further comprising regenerating a canola plant from the canola plant cell, wherein the canola plant comprises the nucleic acid of interest.

20. The method of claim 19, wherein regenerating a canola plant from the canola plant cell comprises inducing formation of one or more shoots from an explant comprising the canola plant cell and cultivating at least a first shoot into a whole fertile canola plant.

21. The method of claim 19, wherein regeneration occurs by organogenesis.

22. The method of claim 1, further comprising growing the bacterium other than *Agrobacterium* sp. in an induction medium comprising carbon sources which minimize polysaccharide production during growth in induction medium.

23. The method of claim 22, wherein the carbon source(s) used to minimize polysaccharide production during growth in induction medium is glucose in AB-TY medium, or L-arabinose and potassium gluconate in ATA medium.

* * * * *

SEQUENCE LISTING

<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gagagtttga tcctggctca g                                                    21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
aaggaggtga tccagccgca g                                                    21

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
acaataatgt gtgttgttaa gtcttgttgc                                      30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctcaaaccta cactcaatat ttggtgag                                        28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
agatctggct cgcggcggac gcac                                            24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cgctcgcgtc attctttgct ggag                                            24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tcagcaggat gacgccgtta tcg                                             23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tctcgcccga ccaataccaa cac                                             23

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gctgacgggc ccggatgaat gtcagctact g                                31

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gctctagaaa ttgtaagcgt taataattca gaagaactcg tc                    42

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
caattgcatt tggctcttaa ttatctgg                                    28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gcatgcccga tcgcgctcaa gtaatc                                      26

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
tctaggtccc cccgcgccca tcg                                         23

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ccatggatct ttctggcaat gagaaatc                                    28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15

```
gtcaaaagct gttgacgctt tggctacg                                              28

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
acgggagagg cggtgttagt tgc                                                   23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cgatagcgac aatgccgaga acg                                                   23

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
atgcccgatc gagctcaagt tatc                                                  24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
tgaaaggaca cctctccgtt gctg                                                  24

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ccatggatcc gaaggccgaa ggcaatg                                               27

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
```

```
ctacagactg tttacggttg ggc                                            23
```

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22

```
gtgagcaaag ccgctgccat atc                                            23
```

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23

```
tagagcgtct gcttggttaa acc                                            23
```

<210> SEQ ID NO 24
<211> LENGTH: 1490
<212> TYPE: DNA
<213> ORGANISM: A. tumefaciens

<400> SEQUENCE: 24

```
tagaaaggag gtgatccagc cgcaggttcc cctacggcta ccttgttacg acttcacccc      60
agtcgctgac cctaccgtgg ttagctgcct ccttgcggtt agcgcactac cttcgggtaa     120
aaccaactcc catggtgtga cgggcggtgt gtacaaggcc cgggaacgta ttcaccgcag     180
catgctgatc tgcgattact agcgattcca acttcatgca ctcgagttgc agagtgcaat     240
ccgaactgag atggcttttg gagattagct cgacatcgct gtctcgctgc ccactgtcac     300
caccattgta gcacgtgtgt agcccagccc gtaagggcca tgaggacttg acgtcatccc     360
caccttcctc tcggcttatc accggcagtc cccttagagt gcccaactaa atgctggcaa     420
ctaagggcga gggttgcgct cgttgcggga cttaacccaa catctcacga cacgagctga     480
cgacagccat gcagcacctg ttctggggcc agcctaactg aaggacatcg tctccaatgc     540
ccatacccdg aatgtcaaga ctggtaagg ttctgcgcgt tgcttcgaat taaaccacat      600
gctccaccgc ttgtgcgggc cccgtcaat tcctttgagt tttaatcttg cgaccgtact      660
ccccaggcgg aatgtttaat gcgttagctg cgccaccgaa cagtatactg cccgacggct     720
aacattcatc gtttacggcg tggactacca gggtatctaa tcctgtttgc tccccacgct     780
ttcgcacctc agcgtcagta atggaccagt aagccgcctt cgccactggt gttcctccga     840
atatctacga atttcacctc tacactcgga attccactta cctcttccat actcaagata     900
cccagtatca aaggcagttc cgcagttgag ctgcgggatt tcacccctga cttaaatatc     960
cgcctacgtg cgctttacgc ccagtaattc cgaacaacgc tagcccccdtt cgtattaccg    1020
cggctgctgg cacgaagtta gccggggctt cttctccgac taccgtcatt atcttcatcg    1080
gtgaaagagc tttacaaccc taaggccttc atcactcacg cggcatggct ggatcaggct    1140
tgcgcccatt gtccaatatt ccccactgct gcctcccgta ggagtttggg ccgtgtctca    1200
gtcccaatgt ggctgatcat cctctcagac cagctatgga tcgtcgcctt ggtaggcctt    1260
taccccacca actagctaat ccaacgcggg ctcatccatc ccgataaat ctttccccg      1320
```

```
tagggcgtat gcggtattaa ttccagtttc ccagagctat tccgcagaga tgggtagatt    1380
cccacgcgtt actcacccgt ctgccactcc ccttgcgggg cgttcgactt gcatgtgtta    1440
agcctgccgc cagcgttcgt tctgagccag gatcaaactc tcaagttgag               1490
```

<210> SEQ ID NO 25
<211> LENGTH: 1366
<212> TYPE: DNA
<213> ORGANISM: Rhizobium leguminosarum

<400> SEQUENCE: 25

```
cttcgcccag tcgctgaccc kascgkggtt agctgsctcc kkgcggttag cgcactacct      60
tcgggtaaaa ccaactccca tggtgtgacg ggcggtgtgt acaaggcccg ggaacgtatt     120
caccgcggca tgctgatccg cgattactag cgattccaac ttcatgcact cgagttgcag     180
agtgcaatcc gaactgarat ggcttttgga gattagctca cactcgcgtg ctcgctgccc     240
actgtcacca ccattgtagc acgtgtgtag cccagcccgt aagggccatg aggacttgac     300
gtcatcmcca ccttcctctc ggcttatcac cggcagtccc cttagagtgc ccaactgaat     360
gctggcaact aagggcgagg gttgcgctcg ttgcgggact taacccaaca tctcacgaca     420
cgagctgacg acagccatgc agcacctgtg tcccggtccc cgaagggaac cttgcatctc     480
tgcaagtagc cgggcatgtc aagggctggt aaggttctgc gcgttgcttc gaattaaacc     540
acatgctcca ccgcttgtgc gggcccccgt caattccttt gagttttaat cttgcgaccg     600
tactccccag gcggaatgtt taatgcgtta gctgcgccac cgaacagtat actgcccgac     660
ggctaacatt catcgtttac ggcgtggact accagggtat ctaatcctgt ttgctcccca     720
cgctttcgca cctcagcgtc agtaatggac cagtgagccg cctcgccac tggtgttcct     780 ccgaatatct acgaatttca cctctacact cggaattcca ctcacctctt ccatactcca     840
gatcgacagt atcaaaggca gttccagggt tgagccctgg gatttcaccc ctgactgatc     900
gatccgccta cgtgcgcttt acgcccagta attccgaaca cgctagcccc cttcgtatt      960 accgcggctg ctggcacgaa gttagccggg gcttcttctc cggataccgt cattatcttc    1020
tccggtgaaa gagctttaca accctagggc cttcatcact cacgcggcat ggctggatca    1080
ggcttgcgcc cattgtccaa tattccccac tgctgcctcc cgtaggagtt tgggccgtgt    1140
ctcagtccca atgtggctga tcatcctctc agaccagcta tggatcgtcg ccttggtagg    1200 ccttttacccc accaactagc taatccaacg cgggctcatc cttgaccgat aaatctttct    1260
cccgaaggac acatacggta ttagcacaag tttccctgcg ttattccgta gtcaagggta    1320
gattcccacg cgttactcac ccgtctgccg ctccccttgc ggggcg                   1366
```

<210> SEQ ID NO 26
<211> LENGTH: 1323
<212> TYPE: DNA
<213> ORGANISM: Rhizobium leguminosarum

<400> SEQUENCE: 26

```
agcgcactac ctctcgggta aaaccaactc ccatggtgtg acgggcggtg tgtacaaggc      60
ccgggaacgt attcaccgcg gcatgctgat ccgcgattac tagcgattcc aacttcatgc     120
actcgagttg cagagtgcaa tccgaactga gatggctttt ggagattagc tcacactcgc     180
gtgctcgctg cccactgtca ccaccattgt agcacgtgtg tagcccagcc cgtaagggcc     240
atgaggactt gacgtcawca ccaccttcct ctcggcttat caccggcagt cccttagag     300
```

```
tgcccaactg aatgctggca actaagggcg agggttgcgc tcgttgcggg acttaaccca    360
acatctcacg acacgagctg acgacagcca tgcagcacct gtgtcccggt ccccgaaggg    420
accttgcatc tctgcaagta gcgggcatgt caagggctgg taaggttctg cgcgttgctt    480
cgaattaaac cacatgctcc accgcttgtg cgggcccccg tcaattcctt gagttttaat    540
cttgcgaccg tactccccag gcggaatgtt taatgcgtta gctgcgccac cgaacagtat    600
actgcccgac ggctaacatt catcgtttac ggcgtggact accagggtat ctaatcctgt    660
ttgctcccca cgctttcgca cctcagcgtc agtaatggac cagtgagccg ccttcgccac    720
tggtgttcct ccgaatatct acgaatttca cctctacact cggaattcca ctcacctctt    780
ccatactcca gatcgacagt atcaaaggca gttccagggt tgagccctgg gatttcaccc    840
ctgactgatc gatccgccta cgtgcgcttt acgcccagta attccgaaca acgctagccc    900
ccttcgtatt accgcggctg ctggcacgaa gttagccggg gcttcttctc cggataccgt    960
cattatcttc tccggtgaaa gagctttaca accctagggc cttcatcact cacgcggcat   1020
ggctkgatca ggcttgcgcc cattgtccaa tattccccac tgctgcctcc cgtaggagtt   1080
tgggccgtgt ctcagtccca atgtggctga tcatcctctc agaccagcta tggatcgtcg   1140
ccttggtagg cctttacccc accaactagc taatccaacg cgggctcatc cttgaccgat   1200
aaatctttct cccgaaggac acatacggta ttagcacaag tttccctgcg ttattccgta   1260
gtcaagggta gattcccacg cgttactcac ccgtctgccg cttccccttg cggggcgcat   1320
acg                                                                 1323

<210> SEQ ID NO 27
<211> LENGTH: 1341
<212> TYPE: DNA
<213> ORGANISM: Rhizobium leguminosarum

<400> SEQUENCE: 27
ggttagctgc ctccttgcgg ttagcgcact accttcgggt aaaaccaact cccatggtgt     60
gacgggcggt gtgtacaagg cccgggaacg tattcaccgc ggcatgctga tccgcgatta    120
cgaccgattc caacttctag cactcgagtt gcagagtgca atccgaactg agatggcttt    180
tggagattag ctcacactcg cgtgctcgct gcccactgtc accaccattg tagcacgtgt    240
gtagcccagc ccgtaagggc catgaggact tgacgtcatc cccaccttcc tctcggctta    300
tcaccggcag tccccttaga gtgcccaact gaatgctggc aactaagggc gagggttgcg    360
ctcgttgcgg gacttaaccc aacatctcac gacacgagct gacgacagcc atgcagcacc    420
tgtgtcccgg tccccgaagg gaaccttgca tctctgcaag tagccgggca tgtcaagggc    480
tggtaaggtt ctgcgcgttg cttcraatta aaccacatgc tccaccgctt gtgcgggccc    540
ccgtcaattc ctttgagttt taatcttgcg accgtactcc ccaggcggaa tgtttaatgc    600
gttagctgcg ccaccgaaca gtatactgcc cgacggctaa cattcatcgt ttacggcgtg    660
gactaccagg gtatctaatc ctgtttgctc cccacgcttt cgcacctcag cgtcagtaat    720
ggaccagtga gccgccttcg ccactggtgt tcctccgaat atctacgaat tcacctcta    780
cactcggaat tccactcacc tcttccatac tccagatcga cagtatcaaa gcagttcca    840
gggttgagcc ctgggatttc acccctgact gatcgatccg cctacgtgcg ctttacgccc    900
agtaattccg aacaacgcta gccccttcg tattaccgcg gctgctggca cgaagttagc    960
cggggcttct tctccggata ccgtcattat cttctccggt gaaagagctt tacaacccta   1020
gggccttcat cactcacgcg gcatggctgg atcaggcttg cgcccattgt ccaatattcc   1080
```

```
ccactgctgc ctcccgtagg agtttgggcc gtgtctcagt cccaatgtgg ctgatcatcc      1140
tctcagacca gctatggatc gtcgccttgg taggccttta ccccaccaac tagctaatcc      1200
aacgcgggcc gatcctttac cgataaatct ttcccccgaa gggcacatac ggtattagca      1260
caagtttccc tgcgttattc cgtagtaaag ggtacgttcc cacgcgttac tcacccgtct      1320
gccgctcccc ttgcgtggcg c                                                1341
```

<210> SEQ ID NO 28
<211> LENGTH: 1341
<212> TYPE: DNA
<213> ORGANISM: Mesorhizobium loti

<400> SEQUENCE: 28

```
ccttgcggtt agcacagcgc cttcgggtaa aaccaactcc catggtgtga cgggcggtgt      60
gtacaaggcc cgggaacgta ttcaccgcgg catgctgatc cgcgattact agcgattcca     120
acttcatgca ctcgagttgc agagtgcaat ccgaactgag atggcttttg gagattagct     180
cgacctcgcg gtctcgctgc ccactgtcac caccattgta gcacgtgtgt agcccagccc     240
gtaagggcca tgaggacttg acgtcatccc caccttcctc tcggcttatc accggcagtc     300
cccttagagt gcccaactga atgctggcaa ctaagggcga gggttgcgct cgttgcggga     360
cttaacccaa catctcacga cacgagctga cgacagccat gcagcacctg tcaccggtcc     420
agccgaactg aaggtatcca tctctggaaa ccgcgaccgg gatgtcaagg gctggtaagg     480
ttctgcgcgt tgcttcgaat taaaccacat gctccaccgc ttgtgcgggc ccccgtcaat     540
tcctttgagt tttaatcttg cgaccgtact ccccaggcgg aagcttaat gcgttagctg     600 cgccaccgac aagtaaactt gccaacggct agcttccatc gtttacgcg tggactacca      660 gggtatctaa tcctgtttgc tccccacgct ttcgcacctc agcgtcagta ccggaccagt     720
gagccgcctt cgccactggt gttcctccga atatctacga atttcacctc tacactcgga     780
attccactca cctcttccgg actcgagata cccagtatca aaggcagttc cggggttgag     840
ccccgggatt tcacccctga cttaagtatc cgcctacgtg cgctttacgc ccagtaattc     900
cgaacaacgc tagcccccctt cgtattaccg cggctgctgg cacgaagtta gccggggctt     960
cttctacggt taccgtcatt atcttcaccg ttgaaagagc tttacaaccc tagggccttc     1020
atcactcacg cggcatggct ggatcaggct tgcgcccatt gtccaatatt ccccactgct     1080
gcctcccgta ggagtctggg ccgtgtctca gtcccagtgt ggctgatcat cctctcagac     1140
cagctatgga tcgtcgcctt ggtaggccat taccccacca actagctaat ccaacgcggg     1200
ctcatccatc tccgataaat ctttctccaa aaggacgtat acggtattag ctccagtttc     1260
ccggagttgt tccgtagaga tgggtagatt cccacgcgtt actcacccgt ctgccgctcc     1320
ccttgcgggg cacgcgccct t                                                1341
```

<210> SEQ ID NO 29
<211> LENGTH: 1339
<212> TYPE: DNA
<213> ORGANISM: S. Fredii

<400> SEQUENCE: 29

```
agccttgcgg ttagcgcact accttcgggt agaaccaact cccatggtgt gacgggcggt      60
gtgtamaagg cccgggaacg tattcaccgc agcatgctga tctgcgatta ctagcgattc     120
caacttcatg cactcgagtt gcagagtgca atccgaacta gatggctttt ggagattag      180
```

```
ctcgacctcg cggtctcgct gcccactgtc accaccattg tascacgtgt gtagcccagc    240
ccgtaagggc catgaggact tgacgtcatc cccaccttcc tctcggctta tcaccggcag    300
tccccttaga gtgaccaact aaatgctggc aactaagggc gagggttgcg ctcgttgcgg    360
gacttaaccc aacatctcac gacacgagct gacgacagcc atgcagcacc tgtctccgat    420
ccagccgaac tgaaggatac gatctctcgt atccgcgatc gggatgtcaa gggctggtaa    480
ggttctgcgc gttgcttcga attaaaccac atgctccacc gcttgtgcgg gccccgtca     540
attcctttga gttttaatct gcgaccgta ctccccaggc ggaatgttta atgcgttagc     600
tgcgccaccg aacagtaaac tgcccgacgg ctaacattca tcgtttacgg cgtggactac    660
cagggtatct aatcctgttt gctccccacg cttttcgcacc tcagcgtcag taccggacca    720
gtgagccgcc ttcgccactg tgttcctcc gaatatctac gaatttcacc tctacactcg     780
gaattccact caccctcttcc ggactctaga cacccagtat caaaggcagt tccggggttg    840
agccccggga tttcaccct gacttaaatg tccgcctacg tgcgctttac gcccagtaat     900
tccgaacaac gctagcccc ttcgtattac gcgggctgct ggcacgaagt tagccggggc     960
ttcttctccg gttaccgtca ttatcttcac cggtgaaaga gctttacaac cctagggcct   1020
tcatcactca cgcggcatgg ctggatcagg cttgcgccca ttgtccaata ttccccactg   1080
ctgcctcccg taggagtttg gccgtgtct cagtcccaat gtggctgatc atcctctcag    1140
accagctatg gatcgtcgcc ttggtaggcc tttaccccac caactagcta atccaacgcg   1200
ggctcatcct ttcccgataa atctttcccc cgaagggctc atacggtatt agcacaagtt   1260
tccctgcgtt attccgtaga aaagggtaga ttcccacgcg ttactcaccm atctgccgcy   1320
cccccgcrgc gcgctcccc                                                1339

<210> SEQ ID NO 30
<211> LENGTH: 1368
<212> TYPE: DNA
<213> ORGANISM: Bradyrhizobium sp.

<400> SEQUENCE: 30
gaaggtaccg tggccggctg cctacctagc gggttagcgc accgtcttca ggtaaaacca     60
actcccatgg tgtgacgggc ggtgtgtaca aggcccggga acgtattcac cgtggcgtgc    120
tgatccacga ttactagcga ttccaacttc atgggctcga gttgcagagc ccaatccgaa    180
ctgagacggc tttttgagat tgcgaagggg tcgccccta gcatcccatt gtcaccgcca    240
ttgtagcacg tgtgtagccc agccgtaag ggcatgagg acttgacgtc atccccacct      300
tcctcgcggc ttatcaccgg cagtctcctt agagtgctca actaaatggt agcaactaag    360
gacgggggtt gcgctcgttg cgggacttaa cccaacatct cacgacacga gctgacgaca    420
gcatgcagca cctgtgctcc aggctccgaa gagaaggtca catctctgcg accggtcctg    480
gacatgtcaa gggctggtaa ggttctgcgc gttgcgtcga attaaaccac atgctccacc    540
gcttgtgcgg gccccgtca attccttgag ttttaatctt gcgaccgtac tccccaggcg     600
gaatgcttaa agcgttagct gcgccactag tgagtaaacc cactaacggc tggcattcat    660
cgtttacggc gtggactacc agggtatcta atcctgtttg ctccccacgc tttcgtgcct    720
cagcgtcagt atcgggccag tgagccgcct tcgccactgg tgttcttgcg aatatctacg    780
aatttcacct ctacactcgc agttccactc acctctcccg aactcaagat cctcagtatc    840
aaaggcagtt ctggagttga gctccaggat ttcaccctg acttaaagac ccgcctacgc      900
acccttacg cccagtgatt ccgagcaacg ctagccccct tcgtattacc gcggctgctg     960
```

```
gcacgaagtt agccggggct tattcttgcg gtaccgtcat tatcttcccg cacaaaagag    1020
ctttacaacc ctagggcctt catcactcac gcggcatggc tggatcaggg ttgcccccat    1080
tgtccaatat tccccactgc tgcctcccgt aggagtttgg gccgtgtctc agtcccaatg    1140
tggctgatca tcctctcaga ccagctactg atcgtcgcct tggtgagcca ttacctcacc    1200
aactagctaa tcagacgcgg gccgatcttt cggcgataaa tctttccccg taagggctta    1260
tccggtatta gcacaagttt ccctgtgttg ttccgaacca aaaggtacgt tcccacgcgt    1320
tactcacccg tctgccgctg acgtatgctw cgcccgckcg ccckccct                1368
```